US009098114B2

(12) United States Patent
Potter et al.

(10) Patent No.: US 9,098,114 B2
(45) Date of Patent: Aug. 4, 2015

(54) COMPREHENSIVE USER CONTROL SYSTEM FOR THERAPEUTIC WELLNESS DEVICES

(75) Inventors: David Potter, Los Angeles, CA (US); Andrew Norman Corkill, Riverside, CA (US); David Riordan Wood, West Hartford, CT (US); Hans Jorgen Dehli, San Clemente, CA (US)

(73) Assignee: HUMAN TOUCH, LLC, Long Beach, CA (US)

( * ) Notice: Subject to any disclaimer, the term of this patent is extended or adjusted under 35 U.S.C. 154(b) by 202 days.

(21) Appl. No.: 12/876,089

(22) Filed: Sep. 3, 2010

(65) Prior Publication Data

US 2011/0055720 A1  Mar. 3, 2011

Related U.S. Application Data

(60) Provisional application No. 61/239,643, filed on Sep. 3, 2009, provisional application No. 61/299,899, filed on Jan. 29, 2010.

(51) Int. Cl.
*G06F 3/0481* (2013.01)
*G06F 3/01* (2006.01)

(52) U.S. Cl.
CPC .............. *G06F 3/017* (2013.01); *G06F 3/0481* (2013.01); *A61H 2201/5043* (2013.01)

(58) Field of Classification Search
CPC ................. G06F 3/017; G06F 3/0481; A16H 2201/5043; A16H 2201/5046
USPC .......... 715/744–747, 765; 600/300–301, 508, 600/513, 529, 549; 601/16, 118, 137, 148; 128/904, 920; 705/2–4; 345/594
See application file for complete search history.

(56) References Cited

U.S. PATENT DOCUMENTS 7,169,085 B1 *  1/2007  Killin et al. ............... 482/8
2002/0111570 A1  8/2002  Cutler et al.
(Continued)

OTHER PUBLICATIONS

"Panasonic Real Pro Ultra Household Massage Lounger Model EP30006", 2007, Web pages http://www.panasonicmassagechairs.com/EP30006manaual.pdf and www.galtak.com/EP30006k.htm, snapshot of Oct. 22, 2007, and "Panasonic Real Pro Ultra Household Massage Lounger Model EP30006 Operating Instructions", 2007.*
(Continued)

*Primary Examiner* — Claudia Dragoescu
(74) *Attorney, Agent, or Firm* — Christie, Parker & Hale, LLP

(57) ABSTRACT

A comprehensive user control system for use with therapeutic wellness devices is described, comprising such a wellness device, data equipment capable of connection to a data communications network, and a removable data link capable of permitting data communication between the wellness device and data equipment. Other embodiments comprise a general purpose computer capable of connection to a data communications network and programmed to control a wellness device across a removable data link; a method of controlling a wellness device including obtaining over certain data communications connections a program for controlling the device and operating the device in accordance with the program; and a method of controlling a wellness device comprising presentation of a request for therapeutic relief not specifying a particular mechanical action to be performed by the device, and translation of that request into at least one command executable by at least one wellness device.

37 Claims, 21 Drawing Sheets

(56) References Cited

U.S. PATENT DOCUMENTS

| | | | |
|---|---|---|---|
| 2004/0127822 A1* | 7/2004 | Eisenberg | 601/49 |
| 2005/0131273 A1* | 6/2005 | Asano et al. | 600/27 |
| 2006/0026535 A1* | 2/2006 | Hotelling et al. | 715/863 |
| 2006/0146017 A1* | 7/2006 | Leung et al. | 345/156 |
| 2008/0185888 A1* | 8/2008 | Beall et al. | 297/217.4 |
| 2009/0075782 A1* | 3/2009 | Joubert et al. | 482/9 |
| 2010/0017750 A1* | 1/2010 | Rosenberg et al. | 715/803 |
| 2010/0198120 A1* | 8/2010 | Tago et al. | 601/134 |
| 2011/0289455 A1* | 11/2011 | Reville et al. | 715/830 |

OTHER PUBLICATIONS

International Search Report and Written Opinion dated Nov. 9, 2010 for corresponding PCT Application No. PCT/US2010/047916, citing the references listed above (10 sheets).

* cited by examiner

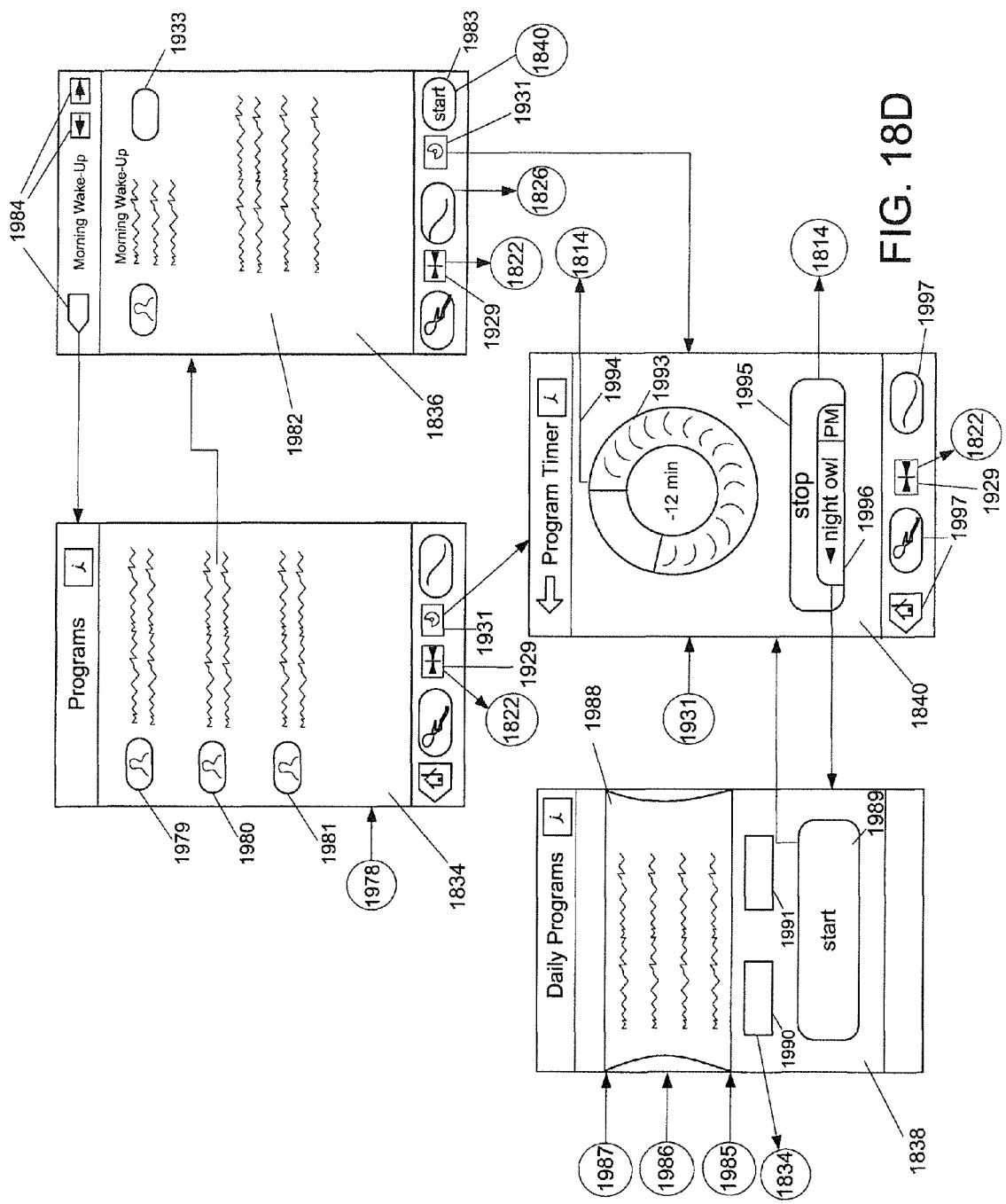

COMPREHENSIVE USER CONTROL SYSTEM FOR THERAPEUTIC WELLNESS DEVICES

CROSS-REFERENCE TO RELATED APPLICATIONS

This application claims the benefit of U.S. Provisional Application No. 61/239,643, filed Sep. 3, 2009, and U.S. Provisional Application No. 61/299,899, filed Jan. 29, 2010, the disclosures of which are incorporated herein by reference.

BACKGROUND OF THE INVENTION

Therapeutic wellness devices such as massage chairs, massage ottomans, vibrators, heating pads, massage pads, aromatherapy devices and various forms of exercise equipment bring relief and relaxation to their users, often using patterns or programs of varying massage or other therapeutic modalities that have traditionally been controlled by a hardwired, handheld control box unit. While the massage and other therapeutic programs delivered by such handheld control units are effective to a degree, they suffer from the limitations of those control units. Only a limited number of massage or other therapeutic programs that can be invoked from the limited numbers of buttons, controls and displays present on such control units. Further, users may not understand how to use such units for optimal effectiveness, or how to translate body condition or complaints into the appropriate or optimal massage or other therapeutic programs. The power and usefulness of these massage and other therapeutic devices can be radically expanded by harnessing the power of distributed computing and computer networks, and also by using sensors and other feedback devices in or associated with the massage or other therapeutic device. These enhancements allow greater flexibility and portability in managing and administering massage and other therapeutic operations, and a shift in emphasis from basic control of simple massage or other therapeutic patterns to comprehensive responses to medical or physiological conditions or situations.

Accordingly, a comprehensive user control system for use with massage or other therapeutic wellness devices is discussed herein, including a preferred embodiment of the present invention comprising an apparatus enabling a connection of massage chairs and other massage or therapeutic wellness devices with wired or wireless external computing units such as personal computers, tablet computers, and smartphones, and with private and public data communications networks such as the Internet. One embodiment comprises a system comprising a therapeutic wellness device and a data link capable of conducting data communication between the therapeutic wellness device and data equipment capable of connection to a data communications network. In various other embodiments, the data equipment comprises a general purpose computer, the data equipment comprises a software application capable or communicating with and controlling the therapeutic wellness device, the data equipment comprises a means for graphically interacting with a user, the data equipment comprises a data communications network, the therapeutic wellness device is a massage chair, and/or the data link is wireless. Other embodiments comprise a program that comprises instructions usable by the therapeutic wellness device and that is communicable across the data link, a program that comprises instructions capable of being used in conjunction with controlling the therapeutic wellness device and that is transferable across a data network. In other embodiments, the therapeutic wellness device is capable of transmitting data over the data link, such as data that pertain to the mechanical condition of the therapeutic wellness device, or that pertain to the usage of the therapeutic wellness device. Another embodiment comprises software residing in the therapeutic wellness device that is capable of being modified by data transmitted across the data link.

Another embodiment in accordance with the present invention comprises a general purpose computer capable of connection to a data communications network, which is programmed to control at least one therapeutic wellness device across a removable data link. In another embodiment, the general purpose computer is portable and the data link is wireless. In other embodiments, the system is configured to maintain a data link with at least one therapeutic wellness device when the system is brought into proximity with that therapeutic wellness device, the system is configured to maintain a data link with at least one of a plurality of models of therapeutic wellness device, and/or the system is configured to convert therapeutic wellness device model-independent information into data compatible with at least one particular model of therapeutic wellness device. In other embodiments, the system is configured to retain data pertaining to at least one user of a therapeutic wellness device, the retained data comprises a user's preferences regarding the operation of the therapeutic wellness device, the system is configured to select at least one particular item of therapy to suggest to a user, and/or the time of day affects a selection of a particular item of therapy to suggest to a user. In other embodiments, the system comprises an interactive graphical user interface, the interactive graphical user interface is configured to comprise displaying an image corresponding to at least a portion of a human body and receiving a user's selection of a portion of said image, the operation of the therapeutic wellness device is determined at least in part by which portion of the image is selected, the interactive graphical user interface is configured to communicate intended benefits from at least one program that is available for selection by a user and that comprises instructions capable of being used in conjunction with controlling a therapeutic wellness device, and/or the therapeutic wellness device is a massage chair.

Other embodiments in accordance with the present invention comprise a method of controlling a therapeutic wellness device comprising obtaining a program that comprises instructions capable of being used in conjunction with controlling the therapeutic wellness device and operating the therapeutic wellness device in a manner corresponding to at least one of the instructions in the program. In certain embodiments, the program is selected from a plurality of programs made available to a user by a general purpose computer programmed to control at least one therapeutic wellness device across a data link, the program is obtained over a data communications network, obtained from a website, obtained from a user of a therapeutic wellness device, obtained from a medical provider, obtained from a source identified with providing programs that comprise instructions capable of being used in conjunction with controlling at least one model of therapeutic wellness device, and/or obtained from a source of supply of at least one model of therapeutic wellness device, and/or the therapeutic wellness device is a massage chair.

Other embodiments in accordance with the present invention comprise a method of controlling a therapeutic wellness device comprising presentation of a request for therapeutic relief that does not specify a particular mechanical action to be performed by a therapeutic wellness device, and translation of the request into at least one command executable by at least one therapeutic wellness device. In another embodiment, the method further comprises transmitting at least one of the request or the at least one command across a data link between data equipment and at least one therapeutic wellness device, and execution of the at least one command by at least one therapeutic wellness device. in another embodiments, the presentation of a request comprises selection of a particular portion of a graphical image corresponding to at least a portion of a human body, pointing to a portion of the user's physical body, and/or presenting information on a condition of a user's body. In other embodiments, an algorithm for performing the translation is selected from among a plurality of available algorithms for performing the translation, and/or the therapeutic wellness device is a massage chair.

Another embodiment of the present invention comprises connections between the massage or other therapeutic wellness device and ancillary devices such as devices for providing additional sensory stimulation, and inclusion of or connections with sensors for reporting of user physiologic data. Another embodiment comprises the use of an interconnected massage or other therapeutic wellness device for control by a local or remote computing device. Another embodiment comprises command of a single massage or other therapeutic wellness device by multiple computing devices or of multiple massage or other therapeutic wellness devices by a single computing device. Another embodiment comprises remote delivery or recording for later user of massage or other therapeutic wellness sequences or programs. Another embodiment comprises integration of massage or other therapeutic wellness programs with audiovisual and multimedia programs. Another embodiment comprises the reporting by the massage or other therapeutic wellness device out to a computer of massage or other therapeutic wellness device data. Another embodiment comprises the use of massage or other therapeutic wellness device sensor feedback for commanding the massage or other therapeutic wellness device by gesture or for medical or therapeutic soothing uses of the massage or other therapeutic wellness device beyond simple short-tem, active massaging or therapy. Another embodiment comprises an exemplary software application for use with the external computing device in controlling and interacting with the massage or other therapeutic wellness device.

BRIEF DESCRIPTION OF THE DRAWINGS

FIGS. 18A through 18D are a chart and screen control flow diagram of user interface screens from an application controlling a therapeutic wellness device.

DETAILED DESCRIPTION

Figure 1:
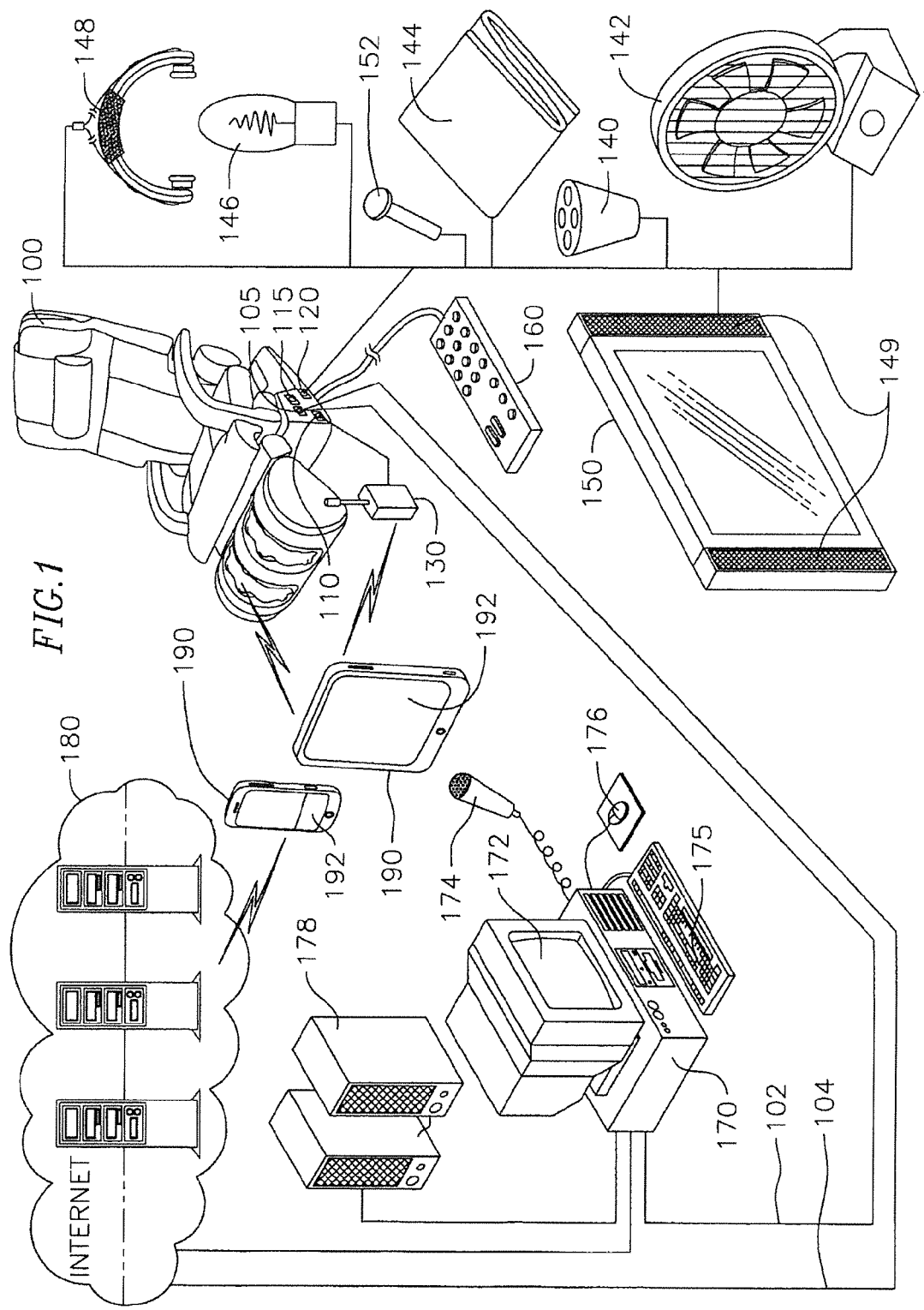
FIG. 1 is a schematic view of a therapeutic wellness device connected to an external computing unit and to ancillary devices.

The detailed description set forth below in connection with the drawing figures illustrations is intended as a description of the presently preferred embodiments of a comprehensive user control system for massage or other therapeutic wellness devices in accordance with aspects of the present invention, and is not intended to represent the only forms in which the present invention may be constructed or utilized. The description sets forth aspects of the comprehensive user control system of the present invention in connection with the illustrated embodiments. It is to be understood that the same or equivalent functions and structures may be accomplished by different embodiments and are also intended to be encompassed within the spirit and scope of the present invention, especially those incorporating a combination of features shown in the different embodiments included herein.

Therapeutic Wellness Devices

The term "therapeutic wellness device" as used herein may refer to any sort of massage device or wellness device or furniture, including without limitation massage chairs, massage ottomans, electronics-driven reclining chairs, other furniture that incorporate electronics or are driven or positioned by actuators or motors, body-part vibrators, heating pads, massage pads, exercise equipment, mood or therapeutic lighting, aromatherapy generators, therapeutic sound machines, therapeutic air movers and ventilators, or any other device that delivers massage, other therapy, or therapeutic benefits to the body. Even in a device such as a massage chair that features traditional massage mechanisms, other, non-massage mechanisms in the device may be manipulated to deliver other types of soothing or wellness benefits. For example, the reclining and positioning mechanisms may be driven to deliver beneficial motion or repetitive motion to the user's body, such as simulating the action of a rocking chair. Thus, although the term "massage device" and illustrations of massage chairs are used in certain embodiments and drawing figures for purposes of exemplary reference, the scope of embodiments of the present invention is not limited to devices that perform massage in the traditional sense, and the use of such examples should are not intended to limit embodiments of the present invention to use with massage devices or massage chairs.

Therapeutic Wellness Device Connections Enabling Communication with External Computing Units, Data Networks and Ancillary Devices Therapeutic wellness devices can be placed and used in the home, office, or other private places. They can also be placed in public settings such as an airport, hotel, or shopping mall, and made available for use on a free or fee basis. Payment for such public use can be on a per-session basis, by subscription, by membership, or on any other fee basis.

One embodiment of the present invention, as depicted in FIG. 1, comprises a therapeutic wellness device 100, whether a massage chair, massage ottoman, or other stand-alone therapy device, comprising an apparatus that can be connected for instance via a wired connection 102 to an external computing unit 170, such as a personal computer, via a wired connection 104 to a public or private local or wide area data network 180 such as a LAN, the mobile telephone network, or the Internet, or via a wireless connection to any device containing a wireless transceiver, such as a tablet computer or smartphone 190. The large array of methods and types of wired and wireless data communications connections are well known to those of skill in the relevant computing and data networking arts.

The connection to the therapeutic wellness device may be established, for example, through use of a wired port 105, 110 such as universal serial bus, or USB port built into the therapeutic wellness device, configured with the therapeutic wellness device as a peripheral device, or other suitable connection. Other useable wired connection schemes include Ethernet ports, and FireWire (IEEE 1394) ports, and standard telephone connection ports. Such wired connections may be implemented using copper, optical fiber, or any other physical transport medium.

As noted above, the data communications connection to the therapeutic wellness device need not be hardwired, but may instead or in addition be wireless, featuring a transceiver inside or connected to the therapeutic wellness device and implementing a wireless RF standard such as Bluetooth, Wi-Fi (IEEE 802.11), ZigBee (IEEE 802.15.4), or GSM (2G), IMT-2000 (3G), or IMT Advanced (4G) mobile telephony. Other useable wireless connections include optical or infrared transceivers. As well, other data communications systems, wired, infrared, optical, RF wireless or otherwise, are likely to be developed in future, and any of them that are suitable for data communications or networking can be used by the embodiments of the present invention. Such a communications connection could be unidirectional, handling either incoming or outgoing data only, or it could be bidirectional, handling both incoming and outgoing data.

The above are just a few examples of data communications connection types and protocols, and any suitable connection, whether wired, infrared, optical, or RF wireless, that can be used for data transmission or networking can be used for this connection; there are many others connection types and many other protocols, such as iPod Accessory Protocol ("iAP") and the Internet Protocol, that may be used with many of these connection types. A large array of additional combinations of protocols and connects are thus usable within the scope and spirit of the present invention, for example communicating with the therapeutic wellness device using iAP running over Bluetooth.

The therapeutic wellness device may have an internal wireless transceiver, one or more external connection ports 105, 110 featuring one or more separate types of connections, or one type of connection may be "piggybacked" onto a different type of connection, for example by converting the therapeutic wellness devices external connection port for use with a different type of wired or wireless connection through use of an external converter or dongle 130.

Connection to and Use of Ancillary Devices

In another embodiment of the present invention, the therapeutic wellness device features additional internal wireless transceiver functionality, an additional internal wireless transceiver, or additional external data communications ports 115, 120, to enable data communications with ancillary or subordinate therapy, display, input, or sensor devices 140, 142, 144, 146, 148, 150, and 152. These ports may also be used to connect to another therapeutic wellness device when a daisy-chain or sharing connection is desired. These ports may be as simple as a pass-through telephone jack, or more complex and independent of the main data communications port. For example, a therapeutic wellness device with a USB data communications port configured as a USB peripheral device may also feature a second, separate USB data communications port 115, 120 configured as a USB host, for separate connection to and communications with ancillary or subordinate devices.

In one embodiment of the present invention, various ancillary or subordinate devices, some of which may themselves also be therapeutic wellness devices, may be present on or connected to the therapeutic wellness device or external computing unit to perform ancillary functions or deliver ancillary services besides the therapy delivered by the therapeutic wellness device. For instance, a white light or colored light device 146 or display screen 150, 172, 192 may be connected or present to deliver a chromatherapy or visual component to the user's experience. (Chromatherapy may alternatively by delivered using the display on the external computing unit or ancillary device display to produce pure colors.) Speakers or headphones 148, 149, 178 may be connected or present to deliver an aural component. Olfactory stimulation such as for aromatherapy purposes may be effected by connection of a volatile material delivery system 140, for example such as described in U.S. Pat. No. 7,490,815 to Tollens et al. Supplemental massage or vibratory stimulation may be delivered by connection of handheld, targeted, or portable vibrator or massager 152, such as a cellulite massager. Heating, cooling, ventilation may be delivered by connection of heating pad 144 or similar heat lamps or heat exchangers, or fan 142 or similar air-movement devices. Such devices and other devices, and/or the therapeutic wellness device itself, may deliver all manner of sensory experience and stimulation, including without limitation any and all of the types of "sensory information" and/or "sensory messages" disclosed in U.S. Pat. No. 7,124,186 to Piccionelli. The devices connected need not be directly involved in providing therapy or sensory stimulation, but may be merely indirectly involved in the user's experience. Other connected devices may include electronically controllable room ambient systems such as room lighting, room ventilation, heating and cooling, window shades, coffee maker, or any other creature comfort or nearby system the user may wish to control as part of or during the time the user is participating in a therapy session. Control of such home automation devices may be accomplished for instance through interface of the external computing unit and/or therapeutic wellness device with home automation systems such as those available from X10 Wireless Technology, Inc. of Seattle.

In another embodiment of the present invention, other wellness devices, or computing units running applications pertaining to such devices, may be connected to the external computing unit or to the therapeutic wellness device for purposes of administering a multidisciplinary wellness program for the user. Such connection may permit exchange of information or direct control in either direction.

Figure 10:
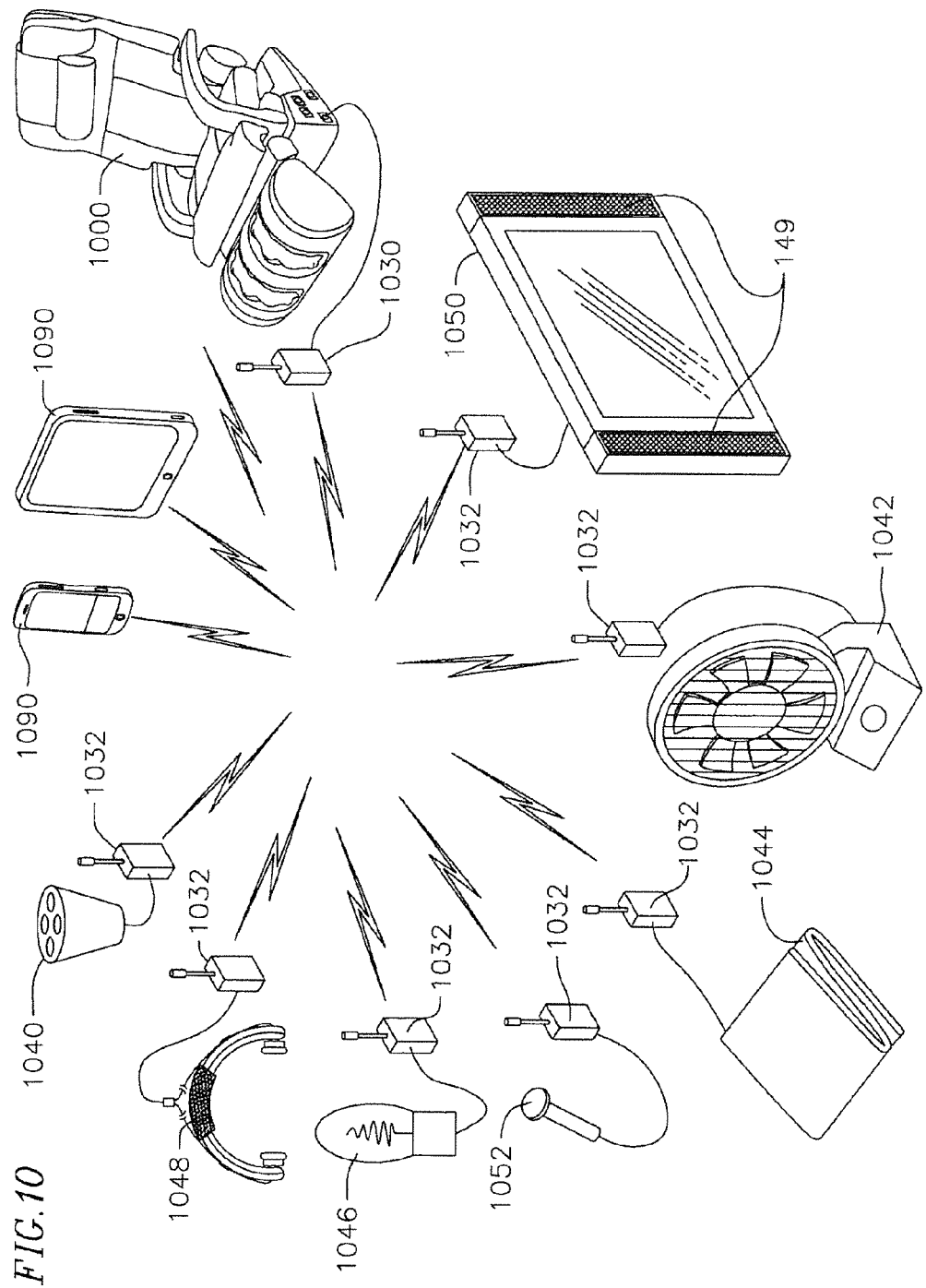
FIG. 10 is a schematic view of a therapeutic wellness device connected to an external computing unit and to ancillary devices via a wireless piconet.

The therapeutic wellness device and ancillary devices are depicted in FIG. 1 in a wired network, but all of the connections between the therapeutic wellness device and ancillary devices, as with all data connections described herein, may be wireless as well as wired. Accordingly, FIG. 10 depicts another embodiment of the present invention, in which therapeutic wellness device 1000, wireless external computing device 1090, and ancillary devices 1040 through 1052 are connected together via wireless transceivers 1032 forming a wireless piconet, such as that established under the Bluetooth connection standard. In such an arrangement, the therapeutic wellness device's wireless transceiver may be housed inside therapeutic wellness device 1000 itself or contained in a connected external dongle 1030. Any of the devices may operate as either master or slave on such a piconet.

Internal Apparatus of Therapeutic Wellness Device

Figure 2:
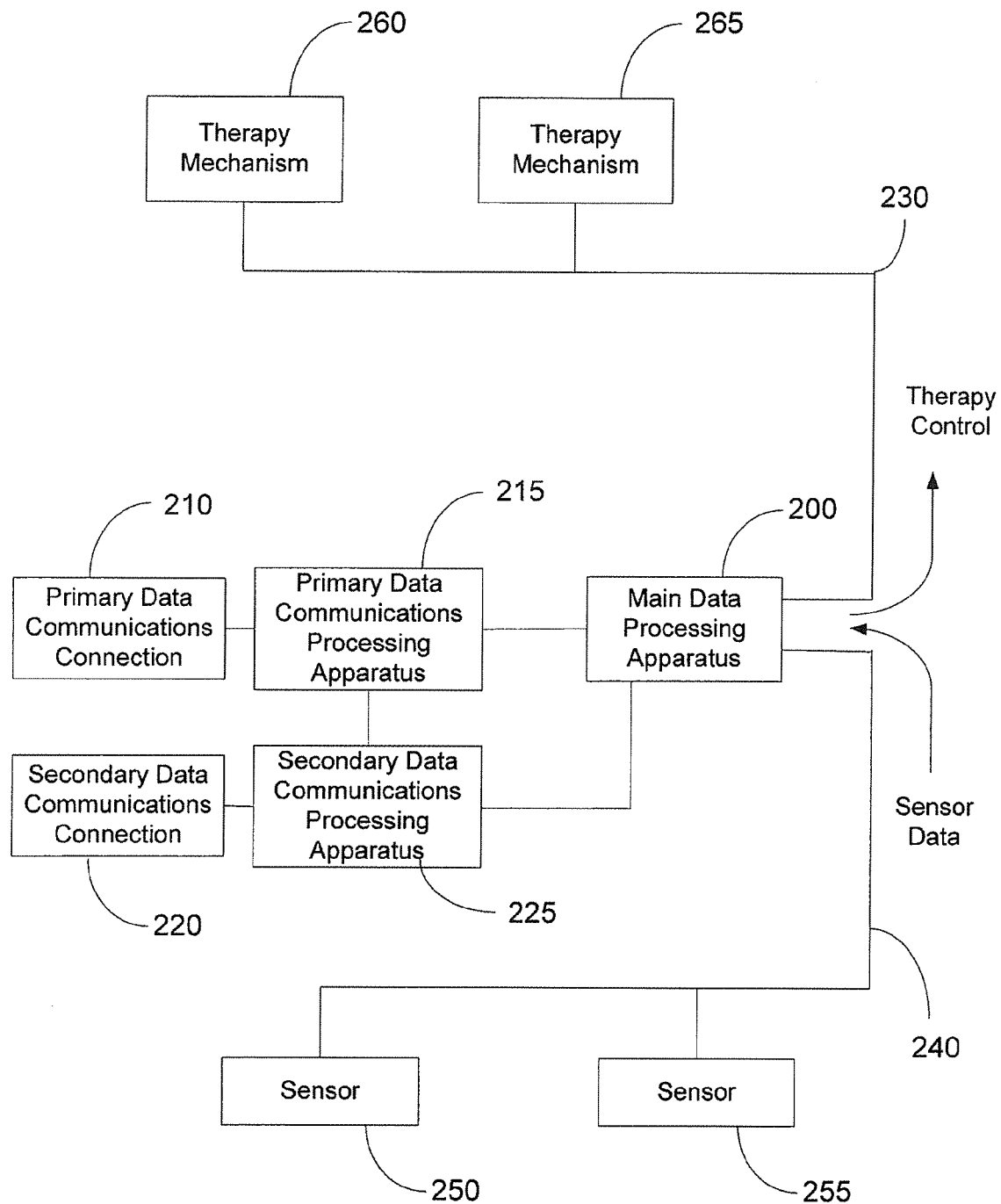
FIG. 2 is a schematic diagram of the internal apparatuses of a therapeutic wellness device in accordance with the present invention.

As depicted in FIG. 2, a therapeutic wellness device in accordance with one or more embodiments of the present invention comprises a primary data communications connection or antenna 210 and primary data communications processing apparatus 215 to receive incoming data from and transmit outgoing data to an external computing unit or data communications network. It further comprises main data processing apparatus 200 to process, convert or interpret incoming data into configurations and operations relevant to therapeutic wellness device operations and to effectuate such configurations and operations by signals via command connection 230 to therapy mechanisms 260, 265 and to positioning mechanisms 270. While for example items such as massage mechanisms and positioning mechanisms are most relevant to massage devices, other equivalent mechanisms for delivering other types of wellness therapy may be employed in addition to or instead of these in other types of therapeutic wellness devices. Main data processing apparatus 200 also processes and interprets data from sensors 250, 255 via data connection 240, as well as therapeutic wellness device and therapy use information and configuration, converting it into outgoing data. A therapeutic wellness device in accordance with the present invention may further comprise a secondary data communications connection or antenna 220 and secondary data communications processing apparatus 225 to receive incoming data from and transmit outgoing data to external ancillary devices or daisy-chained therapeutic wellness devices. The secondary data communications processing apparatus 225 may communicate directly with primary data communications processing apparatus 215 and/or main data processing apparatus 200.

The communications apparatus and/or the data processing apparatus within the therapeutic wellness device can also be used to support, maintain, or enhance the data communications connection itself. Such apparatus may run self-tests on the connection to ensure it is operating properly. Also, in an embodiment featuring a USB or Bluetooth connection, the apparatus or software may support such connection in a "plug-and-play" or inquiry/paging configuration, respectively, to automate the integration of the therapeutic wellness device into the external computing system and eliminate the need for users or operators to manually make connections or specify and install separate software device drivers.

The communications apparatus and the data processing apparatus in a therapeutic wellness device may be, for example, controlled by one or more microprocessors, programmable logic devices, or application-specific integrated circuits. Such data processing apparatus may further feature nonvolatile memory, to permit programs and data to persist in the therapeutic wellness device even if power is removed from the device. In one embodiment of the present invention, the communications apparatus 210, 215, 220 and 225 is integrated with main data processing apparatus 200 and all the apparatus may be implemented together using common hardware and/or software. By contrast, in another embodiment the communications apparatus 210, 215, 220 and 225 is designed and/or implemented separately from main data processing apparatus 200, and may integrated with or retrofitted into an existing unit or model of therapeutic wellness device that has been separately or previously designed or manufactured. Such existing therapeutic wellness device may have been designed to work with a hardwired remote control box, and such a product configuration can be effectively used by embodiments of the present invention.

In one embodiment of the present invention, the software functionality within the communications apparatus and/or the data processing apparatus in the therapeutic wellness device is not permanently fixed and limited at time of manufacture, but may be replaced or upgraded remotely through the data communication connection itself. The specific mechanisms and procedures for such remote firmware or software upgrade or replacement are well known by persons of skill in the relevant computing and data communications arts. Such upgrade or replacement can be initiated and accomplished manually by the user or operator, or remotely over a private or public data network, either under user or operator control or automatically by a manufacturer, distributor, or other software source.

Device Commanding, and Mimicking of Existing Therapeutic Wellness Device Signaling The external computing unit controls the therapeutic wellness device by passing commands to it over the data communications link, and these commands may be interpreted by the therapeutic wellness device's data processing apparatus at various levels. In one embodiment of the present invention, the internal processor architecture of the processing unit can be "exported" to the external computing unit, and low-level elemental commands, even as elemental as individual microcontroller instructions, can be passed to the therapeutic wellness device's processing unit for direct execution by a microcontroller or logic chip in the data processing unit. In another embodiment, by contrast, higher-level or "macro" commands can be passed to the therapeutic wellness device's processing unit whereby a single command can cause the therapeutic wellness device to execute a relatively complex operation or string of operations. Commands may also be of any intermediate level of complexity.

The matching of command levels between the communications processing apparatus for the data link and the therapeutic wellness device's main processing apparatus can be of significant value in the situation where the interface to the data communications link is not manufactured as part of the therapeutic wellness device's main electronics but is instead produced separately from or as a retrofit to the therapeutic wellness device. The use of a higher-level command approach in the data communications link can permit convenient and efficient interface with a therapeutic wellness device that is designed and programmed for use with a wired remote control box. Such a therapeutic wellness device's processing unit is typically programmed to respond to a defined set of higher-level commands, with individual buttons on the wired remote control box typically wired to trigger various of these commands when pressed. In an embodiment using such a higher-level command approach, a data communications processing apparatus can be added or retrofitted to an existing, pre-programmed main processing unit in a therapeutic wellness device. Such a retrofitted apparatus may pass high-level commands to the main processing unit that simulate the button presses on a wired remote control box, but may also increase device functionality beyond that achieved through a wired remote control box, since such apparatus may also pass high-level commands that may not normally have been wired into or associated with a wired remote control box button, or pass combinations or sequences of such high-level "button-simulating" commands beyond those that could be practically generated by pressing individual buttons on a remote control box.

Where the therapeutic wellness device uses a command format such as serial data signaling that is similar in format to the serial data streams typically found in a serial data communications link, the external computing unit can issue commands to the therapeutic wellness device that duplicate or "mimic" the command signaling used by the wired remote control box. This tends to simplify the processing of the command data for use with pre-existing therapeutic wellness device electronics. The data communications processing apparatus in or associated with such a therapeutic wellness device may be constructed as a simpler pass-through signal transceiver for the external computing unit's commands. Such simpler data communications processing apparatus would be capable of providing data signaling employing signals and commands compatible with and expected by the therapeutic wellness device's main data processing unit without the need for extra processing steps or conversion apparatus such as command translation tables.

Figure 11:
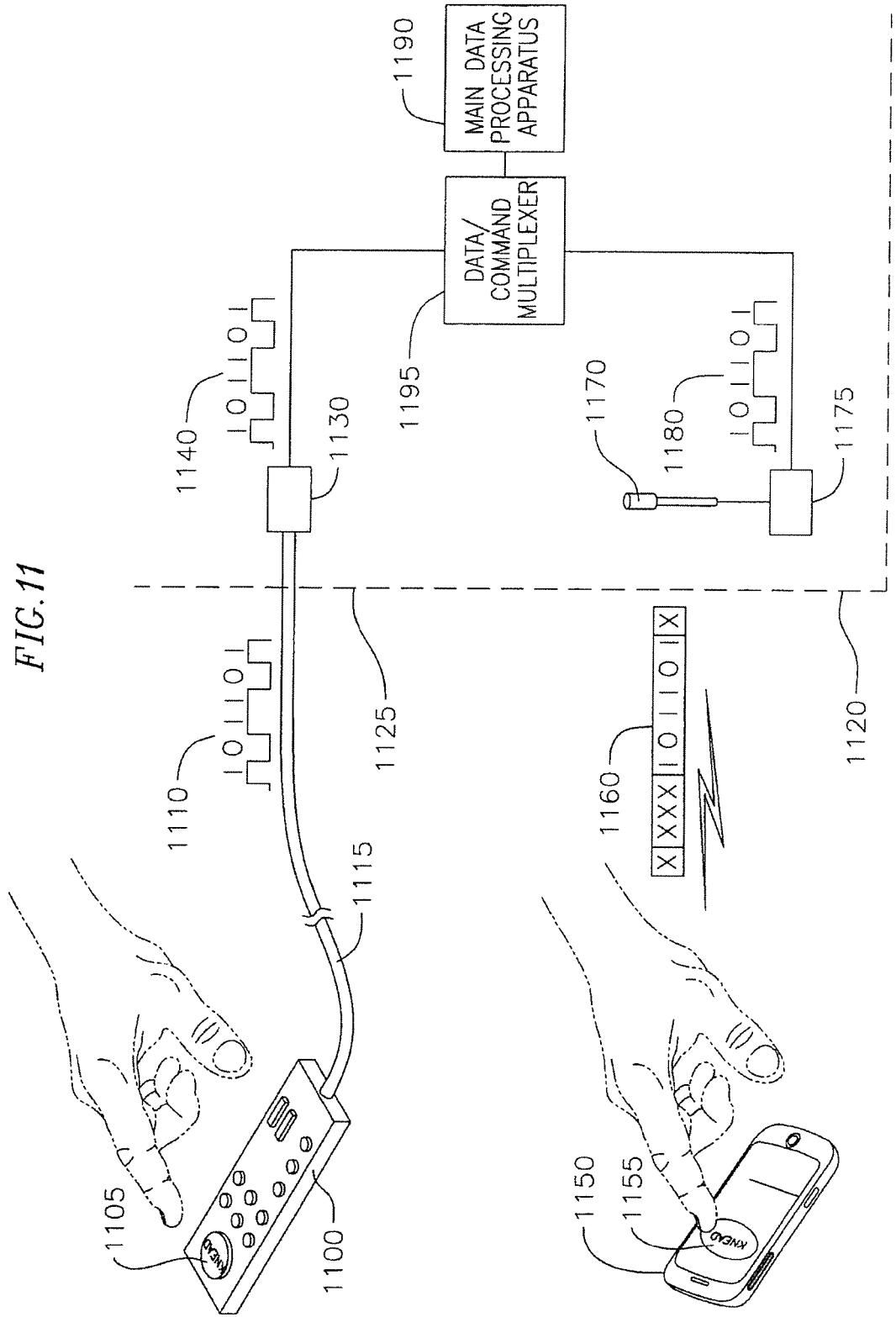
FIG. 11 is a schematic view comparing the transmission of function codes to a therapeutic wellness device's data processing unit via a hardwired remote control box versus a wireless link from an external computing unit.

One embodiment of such a therapeutic wellness device with dual command sources employing mimicking of commands is schematically depicted in FIG. 11. A user pressing a button 1105 on hard-wired remote control box 1100 causes a serial data steam signal 1110 encoded with the unique function code for that button to be sent down the cord 1115 into therapeutic wellness device 1120, where it may optionally be received by a line transceiver 1130 that may condition the signal or adjust its voltage levels to produce serial binary data stream 1140 usable by the data processing apparatus in the therapeutic wellness device. Similarly, a user activating a similar function 1155 on an external computing unit comprising wireless tablet or smartphone device 1150 causes that external computing unit to transmit wirelessly a data packet 1160 containing that same unique function code to the therapeutic wellness device where it is received by wireless transceiver antenna 1170 and fed into wireless transceiver 1175, which does not need to perform any sort of data translation, but needs only to demodulate the wireless RF signal, extract the function code from the data packet, and perhaps condition the signal and set its voltage levels to produce serial binary data stream 1180 usable by the data processing apparatus in the therapeutic wellness device. In a therapeutic wellness device with both command sources, the serial data stream from each control source may be fed into data/command multiplexer 1195 which combines and/or mediates between the incoming data streams and feeds them into the therapeutic wellness device's main data processing apparatus 1190.

As can be seen from FIG. 11, regardless of command source, the therapeutic wellness device's main data processing apparatus operates with the same serial signaling system and same function codes, and is indifferent as to how or where the inputted serial signal originated. Neither the wireless transceiver, line transceiver, nor multiplexer in that therapeutic wellness device need be discrete from the main data processing apparatus, but any of them may merely be functions performed by that apparatus. Conversely, some of those items such as the wireless transceiver and antenna may be physically external to the therapeutic wellness device, such as on a dongle. Although only command input paths are shown in FIG. 11, it should be clear to those of skill in the relevant data communications art that this system may be bidirectional, handling outgoing data from the main data processing apparatus in a similar manner to the commands flowing into it. Further, as noted elsewhere herein, the two command sources may also be communicating between themselves.

Therapeutic Wellness Device Control by External Computing Unit

As illustrated in FIG. 1, a therapeutic wellness device in data communication with either a local or remote external computing unit 170, 190 may be controlled from that unit in addition to or instead of a traditional handheld remote control box 160. Such external computing unit may comprise any sort of computational apparatus. It may for example comprise a general purpose computer loaded with appropriate software, that can be manipulated by user interface devices such as a keyboard 175, mouse 176, or voice recognition apparatus 174 to set modes for or issue commands to the therapeutic wellness device, either the same modes and commands as a handheld remote control box or additional modes or commands, some of which may be too complex to be conveniently issued from a handheld remote control box. It may also comprise any other sort of computing device, for example a personal computer or video game console 170, or a smartphone, personal digital assistant (PDA), portable, laptop, or tablet computer, digital media player, media reader, personal digital assistant, programmable wireless remote control, or similar handheld or mobile device 190. Some examples of such a wireless device include the iPod, iPad, and iPhone products from Apple Inc. of Cupertino, Calif.; products running the Android operating system such as the Droid or Milestone from Motorola, Inc. of Schaumburg, Ill. or the i7500 from Samsung Group of South Korea; products running the Symbian operating system such as the i8910 from Samsung Group; or the BlackBerry from Research in Motion of Canada. A hardware device specifically designed for therapeutic wellness device control, using either wired or wireless data connection, may also be used. Such external computing unit is not limited to microprocessor- or microcontroller-based devices, but may comprise any device capable of computation, whether based on programmable logic devices, application-specific integrated circuits, or any other apparatus.

Figure 12:
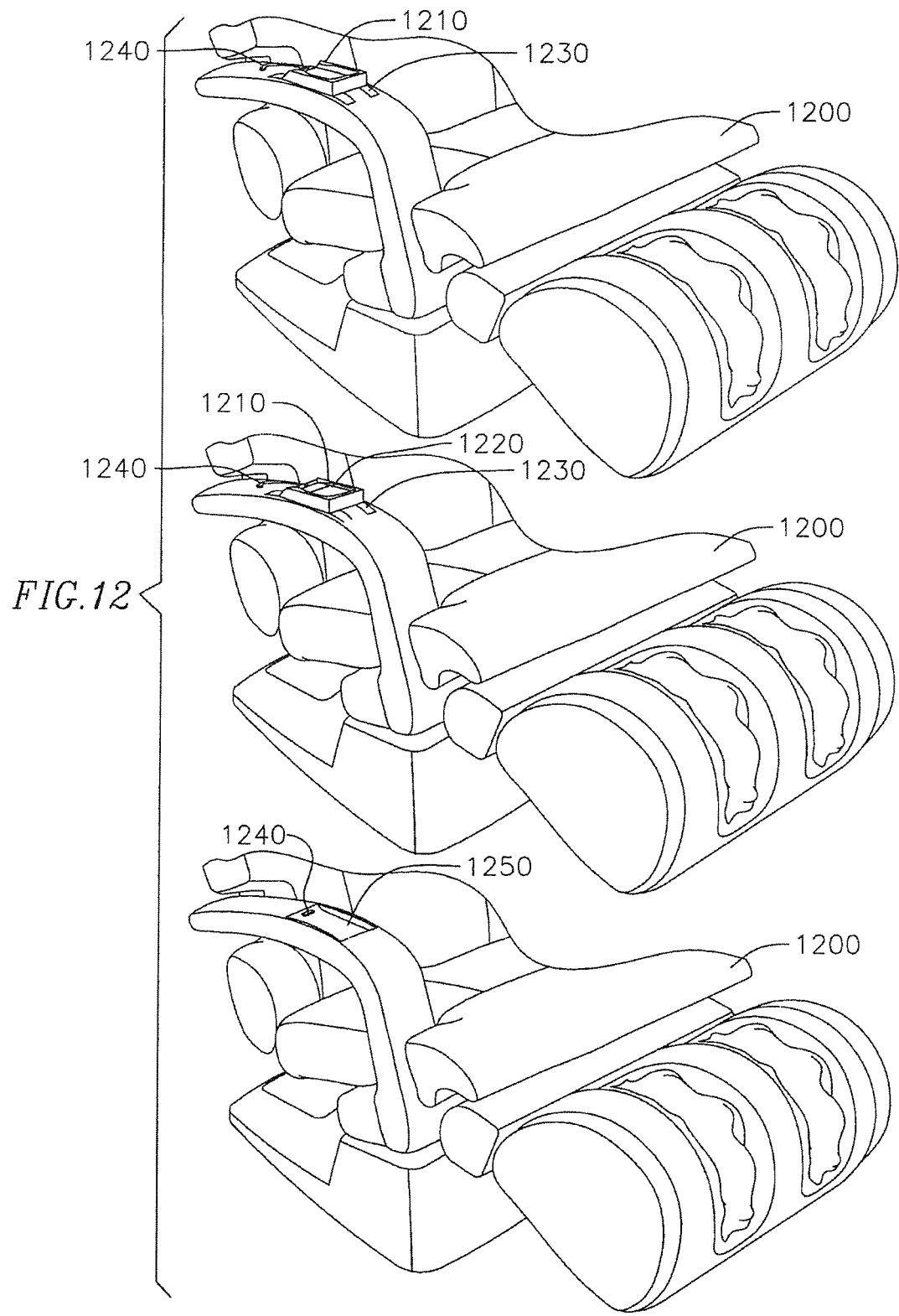
FIG. 12 is a perspective view of a cradle for an external computing unit placed on the armrest of a massage chair.

The external computing unit in one or more embodiments of the present invention may be close enough to the therapeutic wellness device to be used or reached comfortably by a user engaging with the therapeutic wellness device, for example a user sitting in a massage chair or otherwise using a massage device. This is easily accomplished if the external computing unit is a mobile or portable computing or communications device, which the user may hold or place on the device. As illustrated in FIG. 12, therapeutic wellness device 1200, in this illustration a massage chair, contains a cradle 1210 into which portable computing unit 1220 may be placed for easy retention and viewing. In the cradle, the computing unit may lie flat, or may be inclined by the cradle toward the user's viewing angle. The cradle may be permanently affixed or temporarily affixed to the therapeutic wellness device, such as through hook-and-loop fastener strips 1230. The chair may also provide a connection 1240 for the computing unit to provide the unit with data and/or charging power. Alternatively, the cradle may be formed from recess 1250 in the body of the therapeutic wellness device itself. However, the external computing unit need not be in or near the therapeutic wellness device. An external computing unit or an indirectly controlling unit or both may instead be placed remotely from the therapeutic wellness device, at even a long or unlimited distance away.

Although control via an external computing unit 170 or 190 can replace a hardwired handheld remote control box 160, the therapeutic wellness device may also be configured to accept commands from both control sources. The therapeutic wellness device can, for example, respond to the latest command issued from either unit, or be instructed to respond solely to one control source and "lock out" the other source for a period of time or until instructed otherwise, or meld and combine command input from both sources in any other manner or scheme. As well, the external computing unit and the remote control box may each be aware of and accommodate the actions taken by the other control source, for example updating their own status displays when commands or actions taken by the other control source cause the status of the therapeutic wellness device to change; such display updates may originate from the apparatus in the therapeutic wellness device, from each control source sampling or "sniffing" the command data flowing from the other control source, or from data flowing directly between the two control sources. A data connection between the two control sources may also allow additional types of functionality and coordination between them.

In another embodiment of the present invention, a display or the sound emitting capabilities of the external computing unit may be used to assist with command and control of the therapeutic wellness device. The display devices 150, 172 and sound capability devices 148, 178 may be used, for example, to confirm user interaction with the external computing unit or to confirm commands being given to the therapeutic wellness device. The display may be configured simply to imitate the button, control, and display layout of a handheld remote control box, and used with a mouse, screen cursor, and sound capabilities to confirm mouse click selections equivalent to button presses on a remote control box, or the screen and sound capabilities may be configured to convey more complex status and mode information to the user or to other personnel controlling the therapeutic wellness device.

Figure 3:
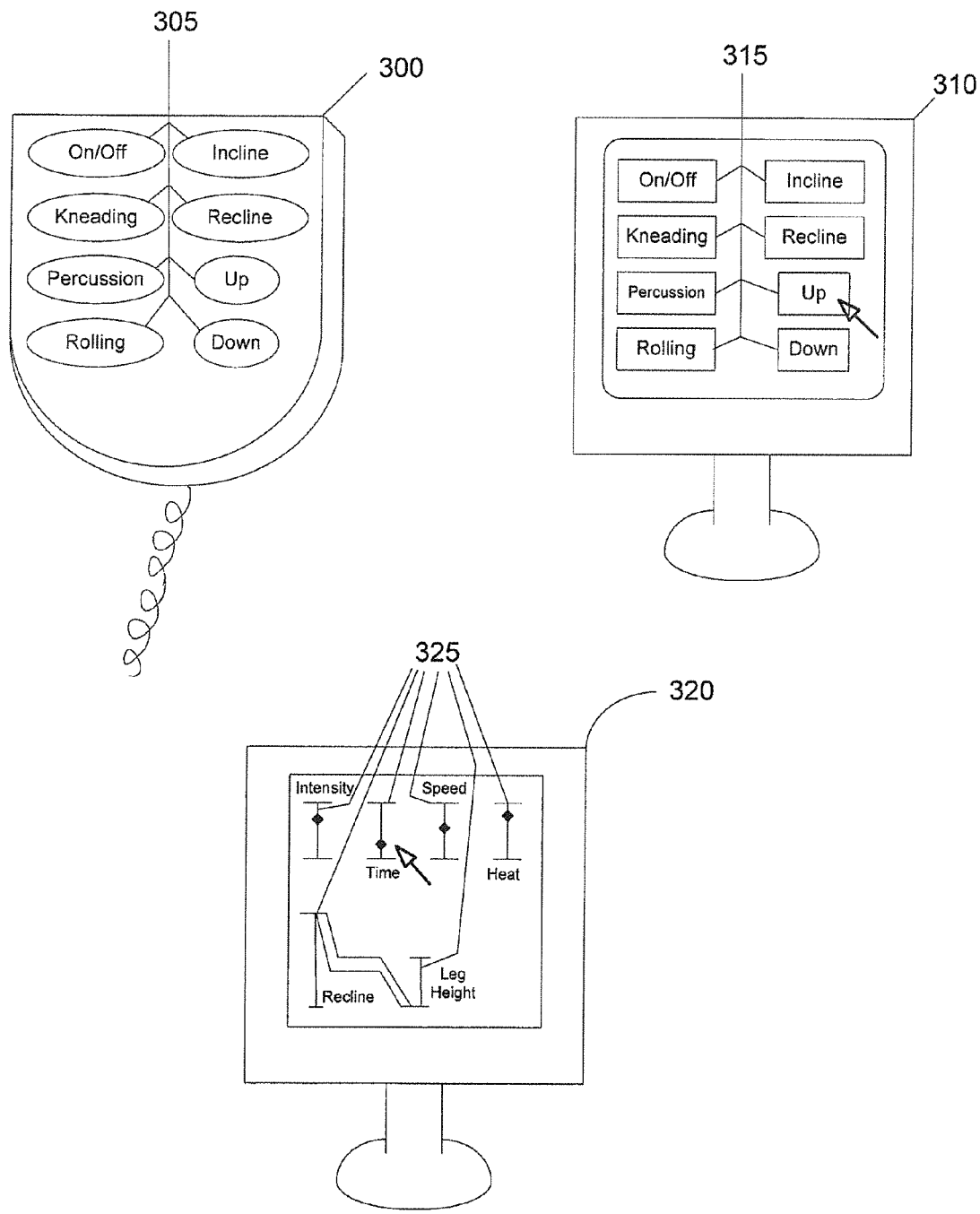
FIG. 3 is an illustration of a traditional handheld control and of various sample display screens in accordance with the present invention.

The external computing unit may be used to issue commands to the therapeutic wellness device that exceed in complexity the relatively simple modes and programs normally commanded from an attached handheld device. Its user interface allows convenient user or operator tracking of complex, high level modes of operation, including complex or custom programs and configurations for the therapeutic wellness device. For example, as illustrated in FIG. 3, instead of or in addition to putting a display 310 into a mode that directly mimics with virtual buttons 315 the physical buttons 305 found on a traditional handheld control 300 to control a therapeutic wellness device, the massage or therapy program or mode could also cause a display 320 to enter a graphical mode, with therapy parameters such as time intervals or intensities of various therapy operations represented by displayed graphical features 325, which may use size, shape, color, curvature or other graphical parameters to convey information. Such a graphical user interface could be interactive, allowing a user to adjust parameters such as intervals or intensities by selecting or dragging displayed graphical objects, for example by graphically depicting the various portions or features of the therapeutic wellness device and allowing the user to drag them into the desired configuration. Other displayed or interactive graphical objects may include a depiction of the human body or its various parts. All these depictions may be either two-dimensional or three-dimensional.

Figure 14:
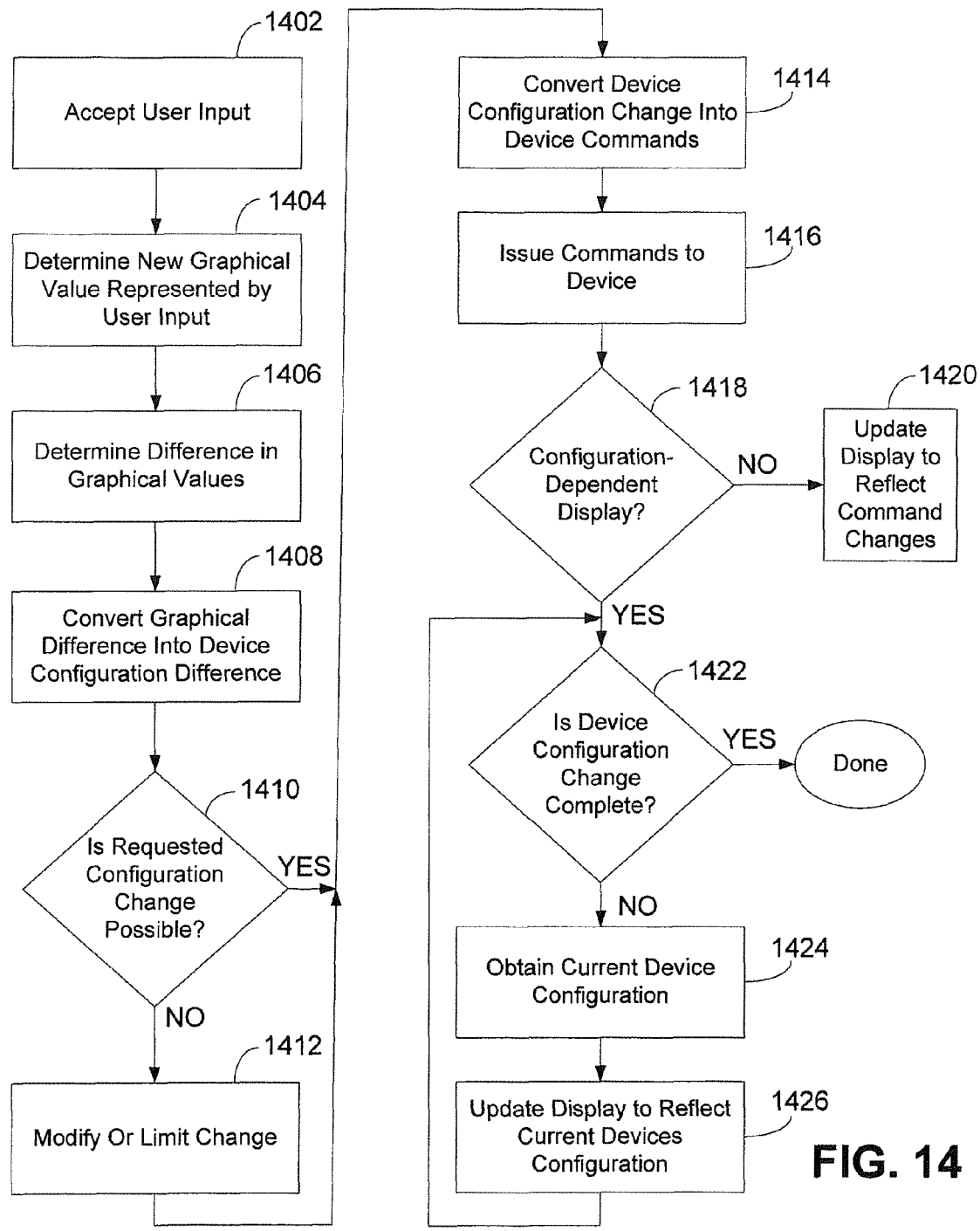
FIG. 14 is a flow diagram showing construction of a command sequence to a therapeutic wellness device based on a user's manipulation of intuitive graphical controls.

In one embodiment, as depicted in FIG. 14, when a user interacts with a graphical display to make a selection, the application accepts (1402) the user input such as selecting or dragging a graphical object, and determines (1404) the new value or position of the graphical object on the display that would be represented by such an input. The application determines (1406) the difference, whether in scalar, vector, or other terms, between the new and old graphical object values. The application converts (1408) the graphical object difference into a configuration difference between the current configuration of the therapeutic wellness device and a new configuration of such device that corresponds to the user's manipulation of the graphical object. Such conversion may be accomplished for example through a lookup table or programmed formula, and may involve the application querying the therapeutic wellness device to determine its current configuration. The application compares (1410) the requested configuration change to the configurations that are possible, and modifies or limits (1412) the configuration change if the requested change would exceed the capability of the therapeutic wellness device, for example, commanding a heating pad to heat to 200 degrees. Generally, the application will modify the change to be the closest possible change to the requested change of which the device is capable. The application converts (1414) the configuration change, modified as necessary, into one or more commands recognizable by the therapeutic wellness device; this conversion also may be accomplished for example through a lookup table or programmed formula. The application issues (1416) the one or more commands to the therapeutic wellness device. It also updates the graphical display; if (1418) the display is not configured to be dependent on the current configuration of the device, the application may simply update (1420) the graphical object on the display to correspond to the user's input, modified as necessary. If, on the other hand, the display is configured to reflect the current configuration of the device, until (1422) the device's configuration change is complete, the application obtains (1424) the device's current configuration in the midst of the change, and updates (1426) the display to reflect the current device configuration. In this way, the display shows the movement of or other change to the therapeutic wellness device in real time as it happens.

Even simple imitation by the external computing unit of a handheld remote control box can be implemented with flexibility surpassing that of a standard hardwired remote control box. For example, the control buttons represented on the screen of the external computing unit can be rearranged by the user or operator via software manipulation for preference or ease of use, or can be made larger to assist users or operators with limited dexterity or eyesight. Voice recognition and audible feedback also can be used to assist visually challenged users or operators.

As compared with standard computing devices using a keyboard or mouse, modern handheld or mobile computing or communications devices featuring a touch screen, such as mobile device 190 with touch screen 192, possess an expanded range of user gestures to which they will recognize and respond, such as sliding, flicking, pinching, finger spreading, tapping, multi-finger tapping, and hand waving. In the case of a massage device, the expanded range of user hand or finger gestures has special usefulness in connection with controlling such a device, due to the intuitive correspondence between many of these gestures and the manual manipulation employed by a massage therapist in giving a massage. For example, a user may make a pinching action to command the massage device to give a massage that employs a pinching action or other mechanical action that simulates a pinching action, the user may make a flicking action to indicate a massage with a flicking or sliding action, a tapping of the fingers to indicate a massage with tapping or pressing action, or a sustained single or multiple finger press to indicate a pressing massage with various widths of contact area. This correspondence of finger action to massage type may be combined with a graphical display, such as a display of a human body or of a massage chair to indicate where the user wishes the requested massage to be applied, for instance making a pinching on the area of the display of a human back representing the upper left shoulder, to command a pinching massage to be applied to the upper left shoulder of the user when sitting in the massage chair. The graphical display of a human body region or of a therapeutic wellness device may also be used in conjunction with user gesturing to translate the location of therapy. For instance, a user who is receiving a particular type of therapy delivered by the therapeutic wellness device to the left side of the user's body may point to or slide toward the right side of a diagram of a human body in order to move that therapy over to the right side. These types of finger gestures have intuitive correspondences to other types of wellness therapies and therapeutic wellness devices aside from massage devices, and may be employed equally effectively with other sorts of therapeutic wellness devices.

Similar to finger or hand gestures, a user may manipulate the portable device itself to command a particular action from the therapeutic wellness device. If the portable device features an accelerometer control, the user may shake or otherwise translate or rotate the portable device in order to issue commands to the therapeutic wellness device, including commands that initiate therapy modes that parallel or are intuitively suggested by the user's motion of the portable device. For example, the user may shake the portable device to command a massage device to instigate a vibrating mode, and the relative amplitude of the shaking may be translated into the relative amplitude of the massage device's vibration, while the relative speed of the shaking may be translated into the relative speed of the vibration. Similarly, the user may tilt the portable device to command a massage device to recline a selected portion of its body-support portions, such as its back support or its leg rest, into the same angle as the tilted portable device. In addition to these examples, any number of other portable device translations or rotations may be assigned to various, perhaps intuitively similar or parallel actions of a therapeutic wellness device.

Use of an external computing unit increases the practical flexibility of programming therapy configurations. Where a particular therapeutic wellness device is used by multiple users, each user may use "presets" or preferences for that particular user. By signaling which user is using the therapeutic wellness device, either by explicit command or by detection of biometric data such as weight, the therapeutic wellness device may assume the configuration preferred by that user. As well, preferences may be defined for various different activities the user may be pursuing while using the therapeutic wellness device, such as massage chair reclining positions for watching television, reading, sleeping, conversation, and the like. Further, preferences may be defined for various body-stressing activities engaged in by the user for which the user seeks therapeutic relief, such as running, golfing, skiing, and the like, or for the physiological or aspirational goals the user may have, such as conditioning, balance, flexibility, or endurance. Preferences as well may be defined for different types or classes of users or for different types of therapy, such as for male or female users. In the case of massage, this may involve various modalities, such as Swedish massages, Tibetan massages, or Hawaiian massages. Still further, preferences may be set on a lower, more mechanical level centering on more basic functionality, for instance preferences among more basic mechanical massage functions like compression, kneading, percussion, and rolling, or particular combinations of them.

Figure 7:
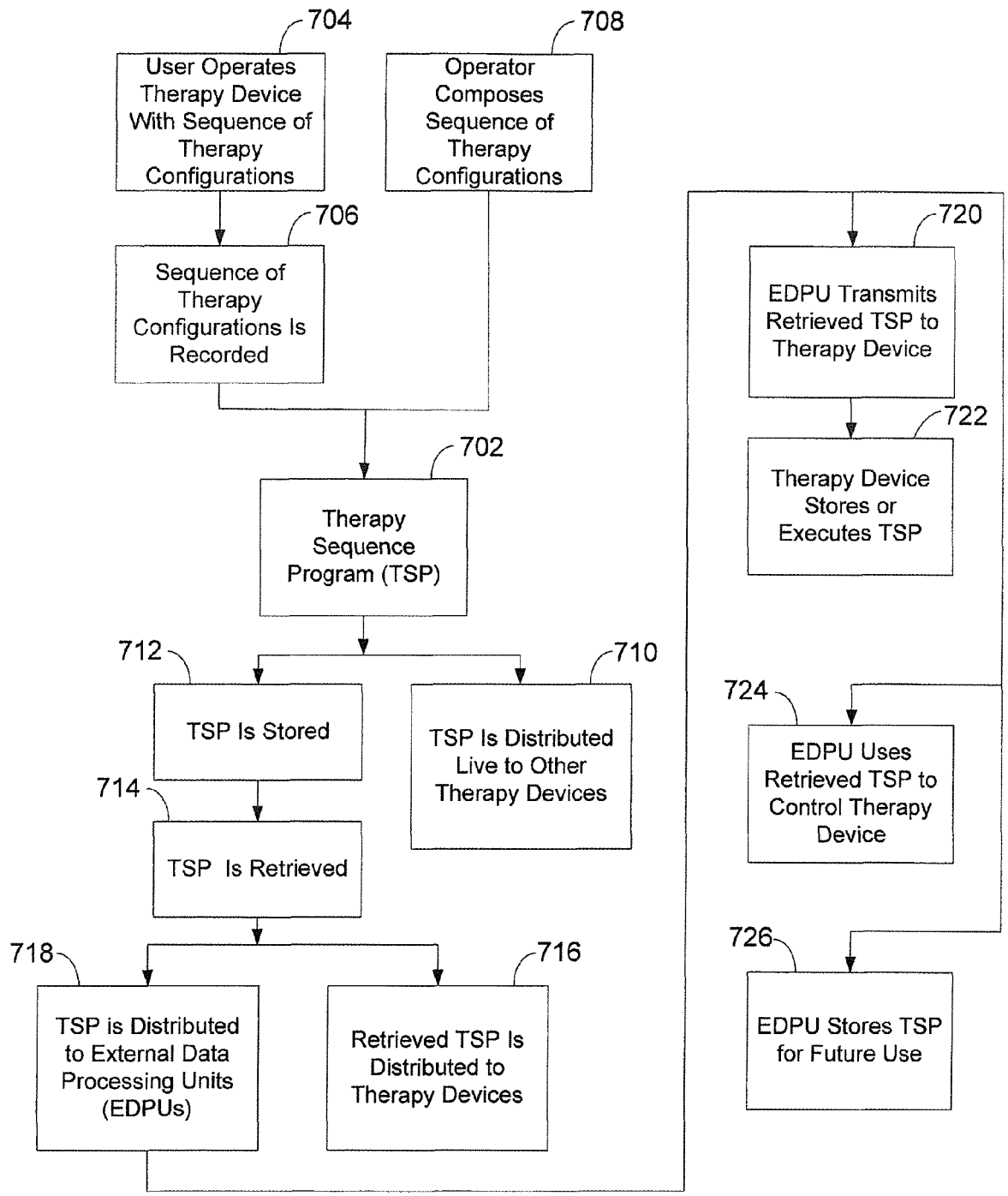
FIG. 7 is a flowchart of the creation, storage and use of a therapy sequence program.

These preferences and presets may be defined and constructed by the user or operator, or they may be composed remotely and distributed to one or more users or operators for "pre-packaged" use. They may be constructed solely from composing and editing commands, or they may use data retrieved or sampled from the configuration of the therapeutic wellness device. An embodiment of a procedure for constructing such therapy preferences and presets as a therapy sequence program is depicted in FIG. 7. To construct a therapy sequence program 702, a user may operate (704) a therapeutic wellness device, putting it through a sequence of therapy configurations, and the sequence of therapy configurations may be recorded (706). Alternatively, an operator may compose (708) a sequence of therapy configurations. As it is being created, or once created, the program may be distributed live (710) in real time for other therapy devices to execute. Alternatively, the program may be stored (712) for later use. Once a stored program is retrieved (714), it may be distributed (716) directly to one or more therapeutic wellness devices for execution. Alternatively, it may be distributed (718) to one or more external data processing units. The external data processing unit or units may in turn transmit (720) the program to a therapeutic wellness device, which may store or execute (722) the program. Alternatively, the processing unit may use and execute the program to control (724) a therapeutic wellness device in carrying out the program. The processing unit may also store (726) the program for future use.

Figure 8:
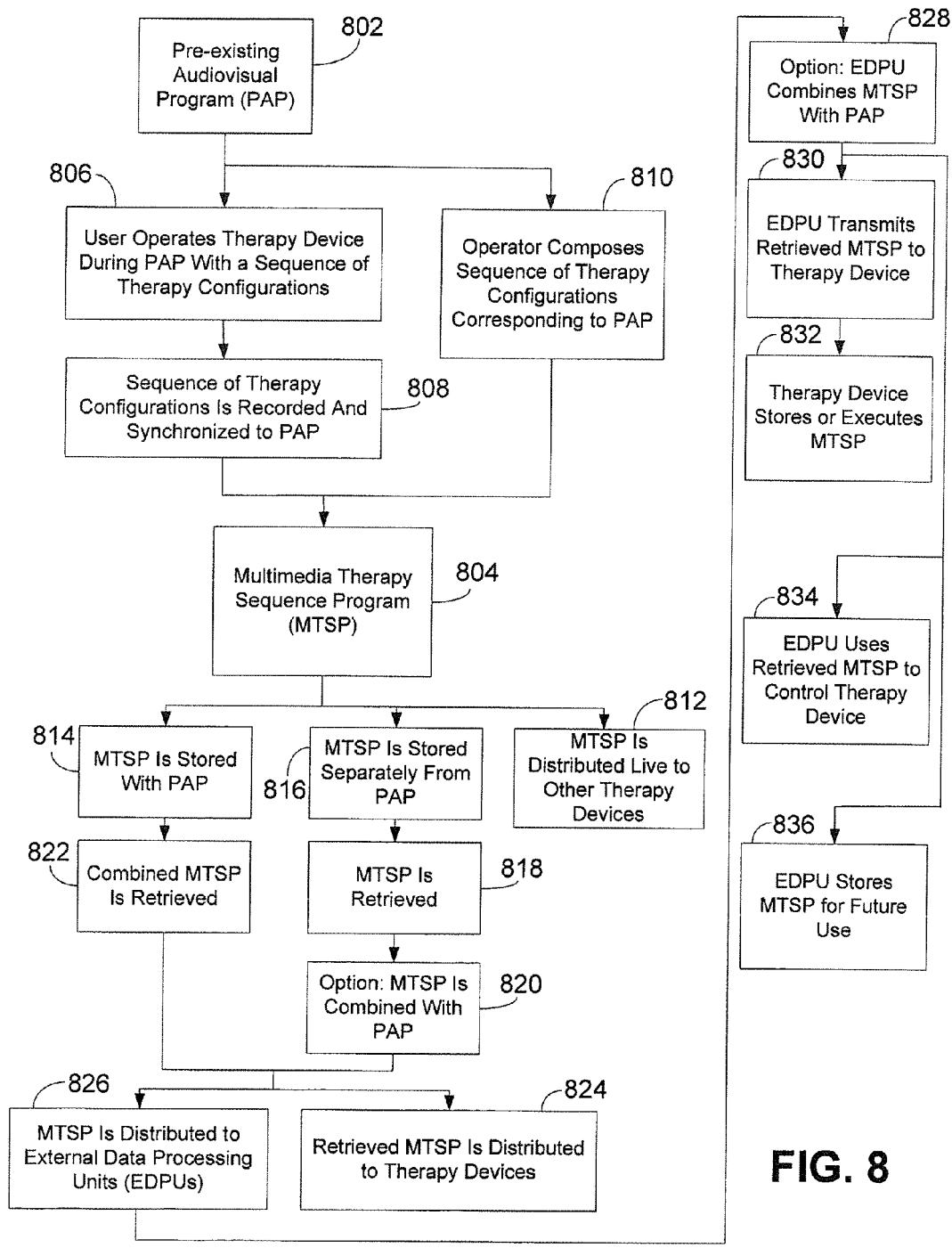
FIG. 8 is a flowchart of the creation, storage and use of a multimedia therapy sequence program.

An embodiment of a procedure for constructing therapy preferences and presets in connection with a pre-existing audiovisual program to construct a multimedia therapy sequence program is depicted in FIG. 8. Starting with a pre-existing audiovisual program 802, a multimedia therapy sequence program 804 may be created by a user operating (806) a therapeutic wellness device, putting it through a sequence of therapy configurations while the audiovisual program is playing, and the sequence of therapy configurations being recorded (808) in synchronism with the audiovisual program. Alternatively, an operator may compose (810) a sequence of therapy configurations in synchronism with the audiovisual program. As it is being created, or once created, the multimedia therapy sequence program may be distributed live (812) in real time in synchronism with the audiovisual program for other therapy devices to execute. Alternatively, the program may be stored either with (814) or separately from (816) the audiovisual program for later use.

A separately stored multimedia therapy sequence program may be retrieved (818) and optionally combined (820) with the audiovisual program, or a program stored with the audiovisual program may be retrieved (822) with it. Once retrieved, the program may be distributed (824) directly to one or more therapeutic wellness devices for execution. Alternatively, it may be distributed (826) to one or more external data processing units. If the program has been stored separately from the audiovisual program and has not already be re-combined with it, they may be combined (828) at the data processing unit. The external data processing unit or units may in turn transmit (830) the program to a therapeutic wellness device, which may store or execute (832) the program. Alternatively, the processing unit may use and execute the program to control (834) a therapeutic wellness device in carrying out the program. The processing unit may also store (836) the program for future use.

Opening up use of a therapeutic wellness device to external programs or content permits the use of programs or content that were not developed for that particular therapeutic wellness device or that were developed for a different therapeutic wellness device, and this may lead to the external computing unit issuing commands to the therapeutic wellness device that concern therapy apparatuses or modes that the therapeutic wellness device does not contain or support, or that the therapeutic wellness device accomplishes differently. To address this issue, in one embodiment of the present invention the external computing unit contains software that translates or transposes the commands to different commands that most closely approximate in the particular therapeutic wellness device the requested operations. In another embodiment of the present invention, such translation or transposition is accomplished by software, firmware, or hardware in the therapeutic wellness device itself. If no roughly equivalent operation exists in the therapeutic wellness device, the command can be ignored, and an alert regarding the ignored command can be passed back to the external computing unit, in order for example to alert the user or to notify the manufacturer of the therapeutic wellness device or the developer of the external computing unit's software.

In another embodiment of the present device, the external computing unit may use computing resources contained within the therapeutic wellness device to share or shed some of the computing load imposed on the external computing unit. For example, an external computing unit whose hardware or software is not capable of or optimal for multitasking may transfer or assign certain of its computing processes or threads over to a processor or processors inside the therapeutic wellness device to promote or permit continuation of multitasking functionality.

The software functionality of an external computing unit controlling a therapeutic wellness device need not be fixed, but instead may be altered or upgraded, and its modes of therapeutic wellness device control changed, by loading new software into the external computing unit. Such software loading may be accomplished manually by the user or operator, or remotely over a private or public data network, either under user or operator control or automatically by a manufacturer, distributor, or other software source.

Remote and Multiple External Computing Units and Therapeutic Wellness Devices

The control of a therapeutic wellness device may come directly from a particular external computing unit, or indirectly, using a multi-hop, daisy-chain, or other data communication topology to permit control from a different external computing unit. For example, a smartphone or similar portable external computing unit may control a therapeutic wellness device directly such as through a Bluetooth wireless connection, while simultaneously in wi-fi or other connection with other computing devices either directly or across a public or private data network. In such a configuration another computing device may be used to control the therapeutic wellness device indirectly through the portable external computing unit, and the external computing unit is usable either to directly relay commands and data from the indirectly controlling device to the therapeutic wellness device, or to interpret, transform or process across formats before sending to the therapeutic wellness device derivative or transformed commands and data. Similar multiple wireless or wired connections may also be used for indirect control where the external computing unit is a larger, desktop computer.

Figure 4:
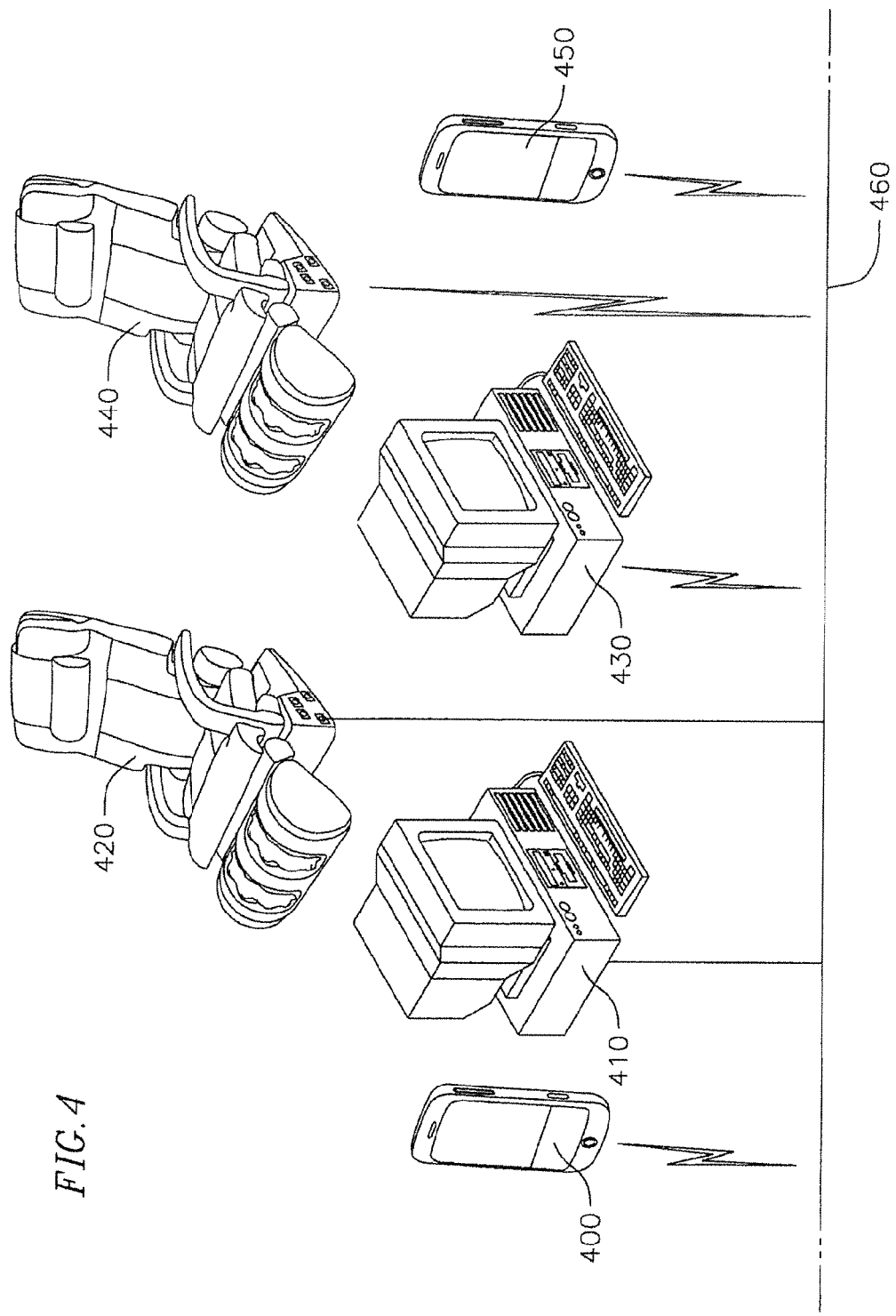
FIG. 4 is a schematic view of therapeutic wellness devices made available as standalone resources on an Ethernet data network.

The therapeutic wellness device need not by directly connected to any one particular external computing unit, and may be controlled directly by multiple various external computing units. For example, in one embodiment of the present invention, as shown in FIG. 4, one or more therapeutic wellness devices 420, 440 may be connected to Ethernet data network 460 and configured to appear as standalone resources on that network, accessible by external computing units 400, 410, 430, and 450 on the network, in a strategy similar to that used in office data networks for standalone printers. As with the combination of an external computing unit and a hardwired remote control box, the therapeutic wellness device may combine or prioritize the commands from multiple control sources in any desired way.

Figure 5:
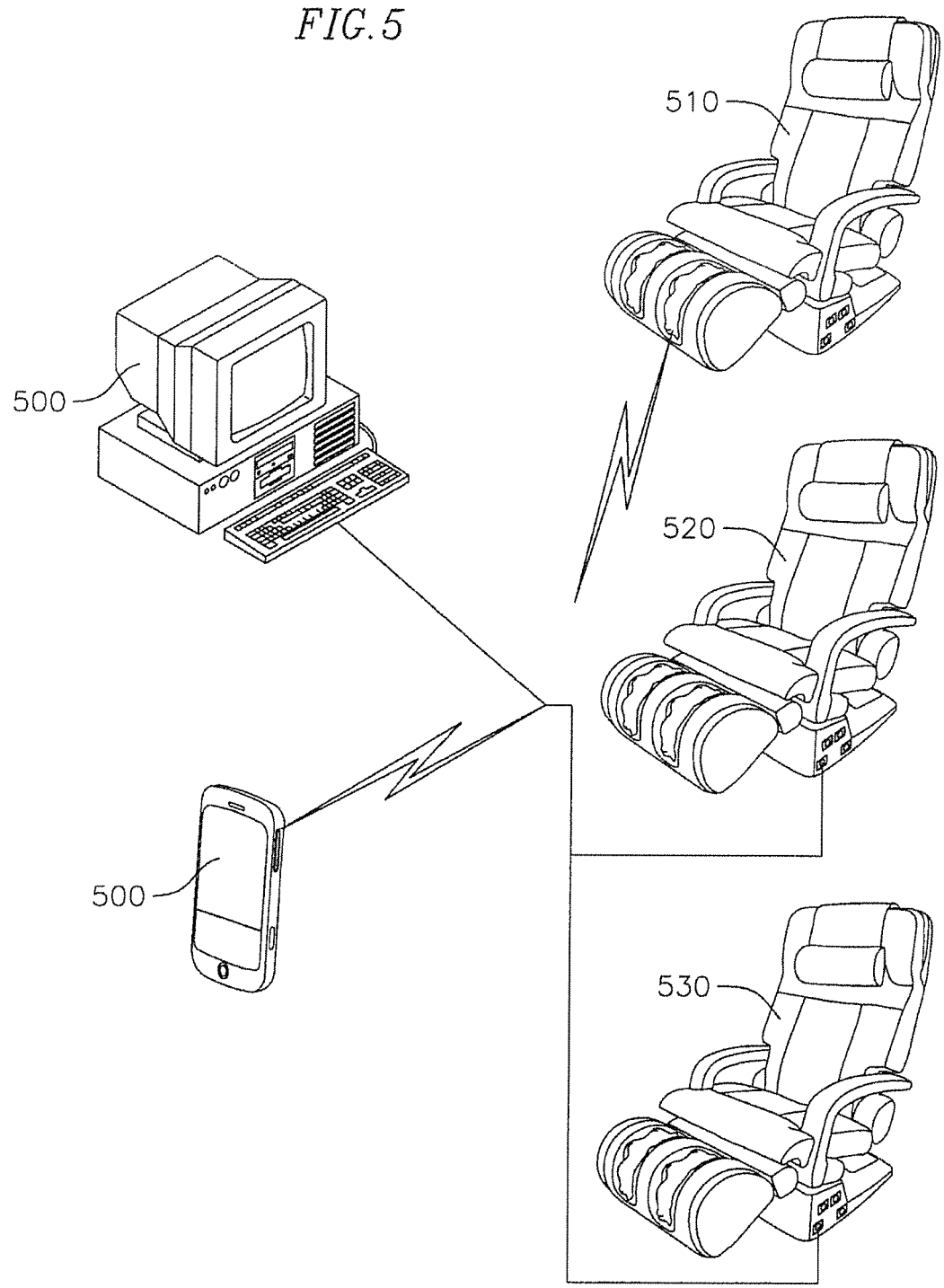
FIG. 5 is a schematic view of a single external computing unit controlling several directly connected therapeutic wellness devices simultaneously.
Figure 6:
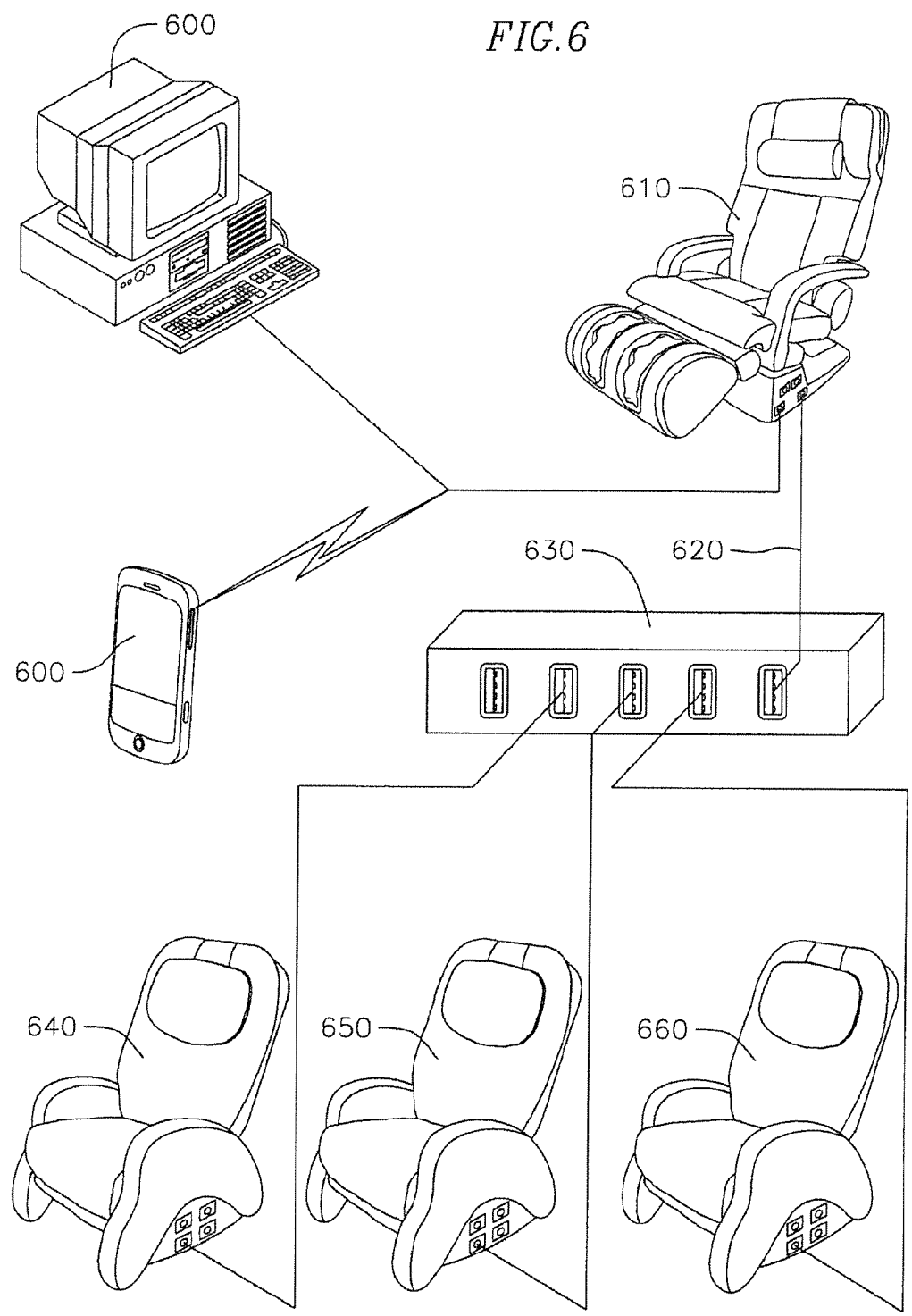
FIG. 6 is a schematic view of a single external computing unit controlling a single directly connected therapeutic wellness device, with several additional therapeutic wellness devices controlled via a secondary connection from the first device.

Just as multiple external computing units may be used to control a single therapeutic wellness device, so also a single external computing unit may be used to control multiple therapeutic wellness devices. In one embodiment of the present invention, as illustrated in FIG. 5, a single external computing unit 500 can be connected to multiple therapeutic wellness devices 510, 520, and 530. Such connection may be made directly via a wired or wireless peer-to-peer data network or piconet, with the therapeutic wellness devices as multiple peripheral units on a data communications loop such as a Universal Serial Bus, or with the therapeutic wellness devices as distributed devices at various locations across a public or private data network. The various therapeutic wellness devices may be controlled either simultaneously or sequentially, with the external computing unit issuing either the same commands to all the therapeutic wellness devices or different commands to various particular therapeutic wellness devices. In another embodiment, as illustrated in FIG. 6, an external computing unit 600 is connected, by wire or wirelessly, directly to a single therapeutic wellness device 610, and that device "clones" or distributes the external computing unit's commands to a group of other therapeutic wellness devices 640, 650, 660 using a secondary distribution network, such as a downstream Universal Serial Bus link 620 and USB hub 630.

The ability to control several therapeutic wellness devices from a single external computing unit has several useful applications. This ability allows a single operator to conveniently stage a group demonstration of the therapeutic wellness devices, such as for promotional or training purposes. Such demonstration, which can be either pre-recorded or "live" in real time, can be controlled remotely, such as over a public or private data network in a "webinar" format. It also finds use in commercial or institutional settings, such as a relaxation class taught by a single instructor, or a medical professional administering therapy to several patients in a hospital, hospice, or rehabilitation facility. The multiple therapeutic wellness devices need not be in a single location, but may be located in diverse, even widely distant, locations, linked through a public or private data network. Similarly, the users of the various simultaneously controlled therapeutic wellness devices need not be in a pre-existing relationship with each other or with the operator of the master controlling external computing unit. For example, a therapy program or relaxation class session may be advertised and made available in broad or public distribution for individual users to subscribe to as they desire, either for free or on a fee basis.

Additionally, two or more therapeutic wellness devices may be linked together, either directly, over a data communications network, or through the use of one or more external computing units, such that the therapy modes and configurations commanded by the user of one therapeutic wellness device are also entered by the other therapeutic wellness device or devices at the same time. In this way a user may share his or her therapy decisions or experiences with other users. This may be accompanied by a "shared screen," where the control screen from one external computing unit may duplicated at the display of a second external computing unit, allowing the second user to see the control steps taken by the first user, and optionally to participate in the control of both devices.

Beyond use of a particular therapeutic wellness device, a user may take defined therapy presets or, as discussed below, defined therapy programs or sequences, and transfer them to other therapeutic wellness devices which the user may use at other locations, including public accommodation therapeutic wellness devices located at hotels, airport lounges, public massage or therapy facilities or kiosks, or on airplanes or other modes of transport. Such transfer may be effected directly across private or public data networks, by use of data-bearing media such as CDs, data cards, or USB flash drives, or by a hybrid transfer device or process such as network data transfer initiated by a card swipe or proximity keychain device. The external computing device may also assist with the user's payment for use of such publicly available therapeutic wellness devices.

Since, as discussed below, some of these presets or programs may induce deep relaxation or sleep, additional parameters may be added to adapt to therapeutic wellness devices used in a public accommodation location, such as a proximity alarm to warn of others approaching the therapeutic wellness device, or an alarm timer to ensure that a user of a therapeutic wellness device in an airport lounge does not miss his or her flight.

In another embodiment, a single portable external computing device may control any number of therapeutic wellness devices at different times, simply by coming into proximity with various such devices, establishing a data connection with them, and exchanging data and issuing commands to them using a standard data format and protocol that the various therapeutic wellness devices understand. The external computing device may maintain its wellness and therapy data and other information in a device-independent format, and as noted herein, either the external computing device or the therapeutic wellness device may interpret that device independent format into commands and other data streams usable by the particular wellness device. In this way a user may carry around the user's personal preferences and programs on a portable external computing device, and receive his or her favorite therapy from any compatible therapeutic wellness device, wherever located. Therapeutic wellness devices may even be "headless," that is, having no intrinsic control device permanently attached to them, and rely instead on a user bringing a portable external computing device into proximity with them in order to perform the necessary control and commanding functions. This may also apply to therapeutic wellness devices in a public place, which as a security measure would not be able to be operated without an appropriate external computing unit, perhaps loaded with an appropriate passcode, being brought into proximity with them.

Therapy Programs or Sequences, and Multimedia Programming Delivery

Programs or sequences of therapeutic wellness device commands for various therapies, such as massage and related activities and configurations, can be defined and used in connection with the external computing unit, which programs or sequences may then be either used by the external computing unit to sequentially command the therapeutic wellness device to assume the various activities and configurations or downloaded to the therapeutic wellness device all at once for later execution by the therapeutic wellness device, or by other therapeutic wellness devices. Such therapy programs or sequences may be composed or defined at the external computing unit. Such composition may be accomplished through the use of a text-based therapeutic wellness device commanding language similar to a programming language. The language may be simple enough for users who are not professional programmers to compose their own therapy programs or sequences. Such composition may alternatively be or additionally be composed using a graphical compiler in which models, maps, or graphical depictions of the therapeutic wellness device may be manipulated to assemble the desired therapy program or sequence. Such therapy programs or sequences may also be defined by a user commanding the therapeutic wellness device to assume the various configurations and activities in a time sequence and simultaneously "recording" or "capturing" such sequence for retention and sharing or later use. Such sequences or programs may be shared via the external computing device and over public or private data networks with others, for example for social purposes with other therapeutic wellness device users or friends by posting to wellness-themed blogs or forums or to social networking sites such as MySpace or Twitter.

Programs or sequences of therapeutic wellness device commands may be downloaded to the external computing unit or directly to the therapeutic wellness device from remote locations. They may be "pulled" by user request, or "pushed" with transmissions originated from the remote location. Remote locations may include websites or electronic facilities maintained by the therapeutic wellness device manufacturer or distributor, or by third-party therapy program developers or providers. Combined with control of multiple therapeutic wellness devices, distribution of audiovisual and therapy programs finds application, for example, in retail promotion to permit audiovisual sales demonstrations of therapeutic wellness devices, or of other products where a therapy session is offered as a marketing inducement, to be conducted simultaneously at several different retail sites. Such distributed audiovisual program in coordination with control of multiple therapeutic wellness devices may take the form of a shared computer screen, so that those using or associated with the controlled therapeutic wellness devices may see the control screen being manipulated at the central control site, for instructional or other purposes. Such a "distributed screen" may further allow those at other sites to participate in the control of such a screen, and thus in the control of one or more of the therapeutic wellness devices.

Figure 15:
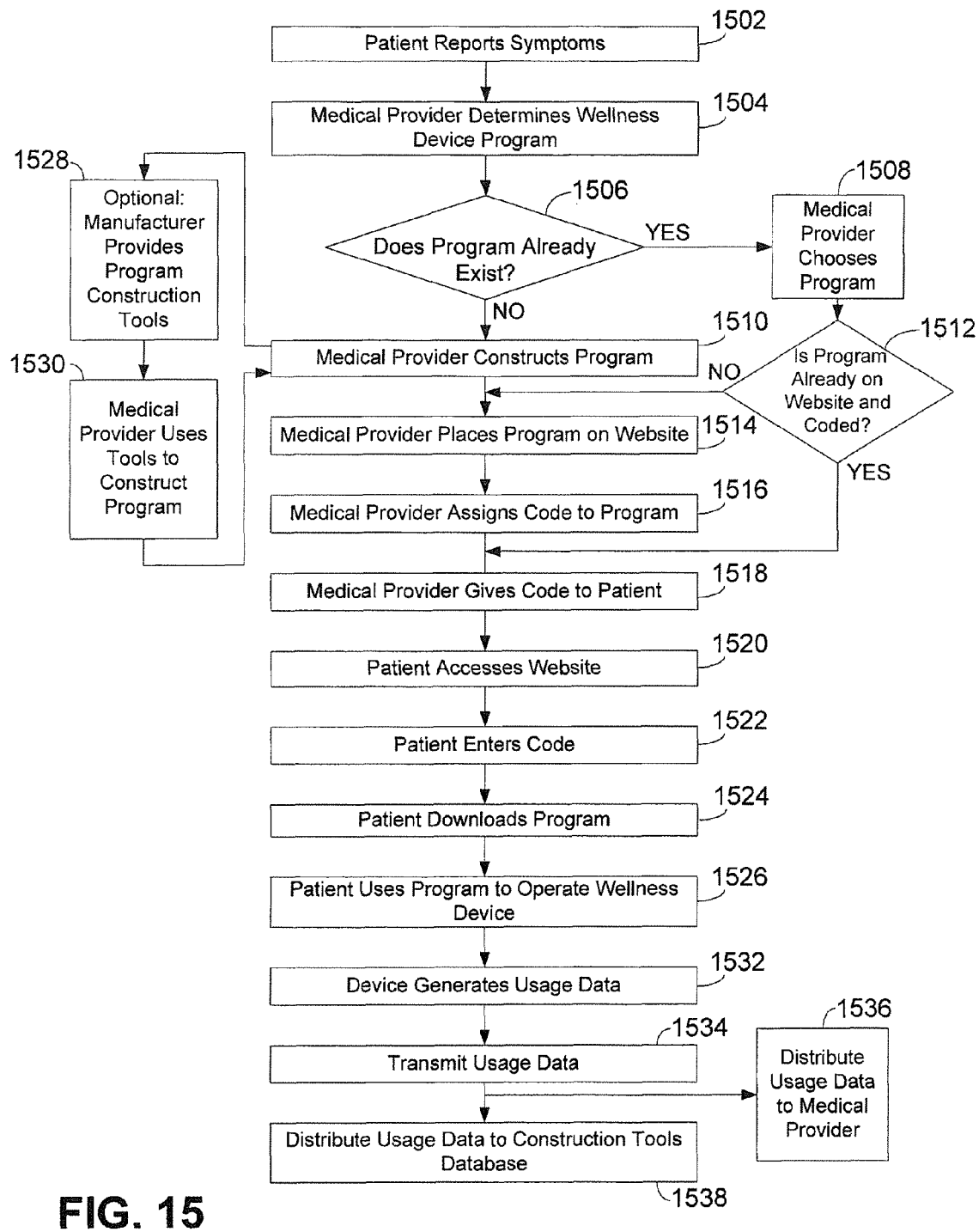
FIG. 15 is a flow diagram showing construction of a therapy program by a medical provider in response to a user's presentation of a complaint or condition.

Such programs or sequences may have general public applicability; for example, "scripts" of massaging sequences preferred or employed by notables in the fitness, therapeutic, or relaxation communities may be made available to the general public. On the other hand, certain programs or sequences may be particularly constructed for a particular user or users. In one embodiment, as depicted in FIG. 15, a patient reports (1502) certain symptoms or conditions to a medical provider. The medical provider determines (1504) particularly for that patient the best specialized program or sequence for a therapeutic wellness device to respond to the reported symptoms or conditions. If (1506) such a program or sequence already exists, the medical provider chooses it (1508). If such a program or sequence does not exist, the medical provider constructs it (1510). Once the new program is constructed, or if (1512) an existing program is not already tagged with a code or password and placed on a publicly accessible data repository, such as a website belonging to the medical provider, the manufacturer or distributor of the therapeutic wellness device or the manufacturer or distributor of the external computing unit application, the medical provider (1514) places the program on the website or other publicly accessible data repository, and assigns (1516) to the program a code or password. The medical provider furnishes (1518) the patient with the code or password for the program or sequence. The patient accesses (1520) the website, inputs (1522) the code or password, downloads (1524) the therapy program or sequence, and uses (1526) the program or sequence to operate the therapeutic wellness device.

In one embodiment, in constructing and following up on such specialized therapy program, the medical professional may be assisted by specialized tools. The manufacturer or distributor of the therapeutic wellness device or external computing unit application, or a third-party provider, may make available (1528) to the medical provider specialized software and databases for therapy program construction. The medical provider may use (1530) these tools for such constructing programs to be executed by therapeutic wellness devices. Such software and database tools may for example include aggregated and historical data on the most effective types of therapy components for various conditions and ailments. They may offer the medical professional a menu of therapy elements from which to construct a customized therapy program for the patient, along with information pertaining to such elements, including medical indications and counter-indications, and data on the efficacy of such elements for particular ailments or conditions. They may also be organized so as to offer particular therapy element suggestions in response to a query concerning a particular ailment or condition.

Such specialized software and databases may further offer the medical professional access to follow-up data from the patient's experience with the prescribed custom program. When using the program prescribed by the medical provider, the therapeutic wellness device may generate (1532) usage data, and this data may be reported or transmitted (1534) manually or automatically by the patient, the patient's therapeutic wellness device, and/or the patient's external computing unit application. Such data may include the patient's schedule of actual usage of the prescribed program, the consistency, regularity, location and other circumstances of such usage, any physiological sensor data collected during such usage, and any self-reported patient condition data in connection with such usage. This data may be sent (1536) to the medical provider for follow up or analysis. This data may also be added (1538) to the program construction tool database for use in influencing future patient therapy program construction.

The programs or sequences downloaded to or executed on a therapeutic wellness device need not be solely devoted to therapy activities. In one embodiment of the present invention, audiovisual or multimedia content may be combined with or augmented by therapy programs or sequences to present a full, multi-sensory experience to the therapeutic wellness device user. Such integration may be fairly loose in synchronization between the audiovisual and therapy programs, for example permitting playing of video content, such as movies or television programs, or music selections, essentially asynchronously either in random sequence or at the selection of the user, during a therapy session. The video or music content may be drawn from the user's current media library, or provided by or licensed from the download provider or third-party media intellectual property owners.

However, the audiovisual or multimedia content may also be tightly integrated with the therapy programs or sequences, allowing execution of a series of therapy operations tightly synchronized in time with the progression of the audiovisual program, creating a synchronized "therapy track" similar to the synchronized soundtrack of a film or video presentation. Such synchronized audiovisual and therapy programs may be produced and distributed by the manufacturer or distributor of the therapeutic wellness device or by third-party providers, or, as noted below, a user may define and "record" a therapy program to synchronize to pre-existing audiovisual content. Such audiovisual content may include relaxation, guided relaxation, yoga, hypnosis, or meditation videos, entertainment, adult entertainment, or travelogue videos, popular music songs or videos, or massage, guided massage, or training videos in the athletic, trainer, chiropractic, or physical therapeutic contexts.

Various sensory components of the multimedia content may be delivered by various devices within, connected to, or ancillary to the therapeutic wellness device, as illustrated by items 140, 142, 144, 146, 148, 150, and 152 in FIG. 1. These devices may be located in or connected to either the computing unit or the therapeutic wellness device, and commanded via the external computing unit or the therapeutic wellness device in conjunction with the therapy, audiovisual, or multimedia program or sequence. Certain aspects of the audiovisual content itself may also be delivered to the therapeutic wellness device for realization, such as low-frequency sound or rumbling to be presented through vibration of the therapeutic wellness device.

In another embodiment of the present invention, the external computing unit and therapeutic wellness device are in communication with a video game, and the audiovisual content is delivered from the video game. In this embodiment, the video game may be running on the external computing unit or on a separate general purpose computer or dedicated video game console. As well, the external computing device may itself be a dedicated video game console. Certain of the audiovisual content and/or control data generated in connection with the video game may be directed for realization by the therapeutic wellness device and/or ancillary devices. For example, an audiovisual component such as rumbling may be optimally presented through vibration of the therapeutic wellness device, and other forms of therapy, such as massage stimulation, may be associated with adult-themed video games. As another example, the recline tilt of a massage chair can translate to the positional attitude of a player in a game. This can flow in either direction; the massage chair's recline tilt commanded by a user can be sent to the game as a command input, or a positional attitude determined within the game can be sent to the massage chair and realized by it as an actual physical tilt. Further, whether or not the video game is running on the external computing unit, that unit can be used as a controller for the video game.

Therapeutic Wellness Device Data Reporting

Data need not flow only from the external computing unit or data network to the therapeutic wellness device, but also in the other direction. In one embodiment of the present invention, the therapeutic wellness device possesses the ability to transmit data out to the external computing unit or data network. This has several uses. For example the therapeutic wellness device can report maintenance data and error codes, either spontaneously or in response to a query from the external computing unit. Such error data may be automatically and directly transmitted to the manufacturer or distributor of the therapeutic wellness device or other service center, or an error report comprehensible to a layman can be given to the user, perhaps including information on contacting customer service by E-mail or other means or with an option that permits the user to transmit the error information immediately to an appropriate service center. Also, data on chair usage, including financial or accounting information, can be captured and reviewed at the external computing unit or uploaded to remote locations. This may include, for example, times and durations of use, frequency of selection of various therapy modes, or the identities of users. This may be used in the commercial context for billing, forecasting, and equipment maintenance purposes, in the institutional or therapeutic context to create logs and records of treatment, and in the personal context for sharing of massage or therapy information with others or for comparison or compliance with massage or therapy plans or recommendations found in wellness books, blogs, or other published or shared material.

More specific data on the specific configuration of the therapeutic wellness device over the course of a therapy session may also be transmitted from the therapeutic wellness device, such data including specific operational details such as specific recline angle, which therapy mechanisms are active and to what intensity, the operation of ancillary sensory stimulation, and ambient details such as room conditions and location of the therapeutic wellness device, as provided by GPS or user self-reporting. This data may be transmitted either in real time as such configurations and operational details change, or in a compiled program of sequential configurations with timestamps showing the duration of each different configuration. In this way, as noted above, a user while using the therapeutic wellness device may define a therapy program or sequence that can be retained and replayed later, either standing alone or in conjunction with and synchronized to an audiovisual or multimedia presentation. As noted above, these therapy or audiovisual programs may be shared with others or published.

Other types and levels of information regarding the user's interaction with the therapeutic wellness device and/or the external computing unit can also be saved, manipulated, and shared. For instance, body metrics or progress milestones in body conditioning, therapy session status or summaries of therapy sessions or experiences, can be shared for diagnostic purposes with health providers, wellness professionals, or shared for social purposes on the same types of blogs, forums or social networking sites as noted above for therapy programs. The user may set up such sharing to occur automatically, for instance setting up a tweet to be issued automatically to the Twitter site whenever the user begins to use or ends use of the therapeutic wellness device, or uses the therapeutic wellness device or external computing unit in a particular manner or mode.

The increased complexity of control made practical by the data communications connection further allows the therapeutic wellness device to be controlled directly at an operational level by third-party computing equipment and software. A therapeutic wellness device manufacturer may publish or make available an application programming interface, or API, comprising a plurality of commands and the protocols and data structures useful for issuing those commands, for instructing the therapeutic wellness device to perform various operations and to report back various information and data. Using such an API, third parties may develop hardware and software that as part of its operation or functionality can directly control a therapeutic wellness device. This may for example promote the integration or combination of therapeutic wellness devices with hardware or software systems that otherwise use audiovisual or other modalities for relaxation or therapy. Such an API may be in addition to, and/or coordinate with, the therapy sequence programming language described elsewhere herein.

Sensor Feedback, Body Gesture Commanding, and Medical/ Therapeutic/Soothing Uses In one embodiment of the present invention, inclusion of sensors in a therapeutic wellness device fitted with the control system adds new dimensions of functionality to the therapeutic wellness device. These sensors, illustrated as 250, 255 in FIG. 2, may be integral to the therapeutic wellness device itself or attached as ancillary devices. Such sensors for example may include handheld devices with buttons or accelerometers, or finger pad or body contact sensors in the top and sides of an armrest or in various body-contact pads or cushions on the therapeutic wellness device that measure localized body pressure, temperature, or galvanic skin response. More advanced physiology sensors may also be used in or with the therapeutic wellness device, including skin-contact and non-contact sensors that measure physiological processes or states such as pulse, respiration, temperature, blood pressure (for example a sphygmomanometer cuff), pulse oxygenation, blood glucose, or neural activity. Such sensors may also include, for use with profoundly disabled users, air-puff sensors or retina movement cameras.

Such sensors may be used directly for commanding the therapeutic wellness device, operating either alone or in conjunction with a cursor and display, such as a display on an external computing unit. For example, a user may move or make gestures with the user's fingers, arms, head or body that are detected by the sensors and used to select a particular therapy mode or issue other commands to the therapeutic wellness device, or to move a cursor around a display and to select commands based on the cursor position. In one embodiment, such sensors may comprise a camera, such as those found on portable telephones and other portable computing devices, and the user's body movements may be captured optically and processed into corresponding gesture commands. The methods for achieving such optical capture are known to those skilled in the art. The cradle recess disclosed herein may be configured to permit a portable device to sit in the armrest of a massage chair or in a similar location on other therapeutic wellness furniture, so as to direct a camera in such device toward the user's body to capture such body movements optically.

The presence of an accelerometer or other position or velocity sensing apparatus in a portable computing or communication device functioning as an external computing unit may be put to good use in conjunction of a therapeutic wellness device that lacks a full complement of position sensors or other means of determine position or movement of the device or of its various parts. Various positional or movement aspects of the therapeutic wellness device, for instance the recline angle of a back rest or the height of the leg rest, may be determined by attaching the mobile device with its accelerometer to that portion of the therapeutic wellness device or of the user's body whose position or movement is to be determined. This can be achieved, for instance, by means of a hook and loop fastener or by affixing a pouch to the therapeutic wellness device into which the portable device is temporarily placed.

The data from sensors on the therapeutic wellness device and/or ancillary devices may also be given directly to the user to guide the therapy experience. Real time data such as temperature and pressure at key ergonomic points can be directly displayed to the user, allowing the user to make body adjustments for optimal comfort or therapy effectiveness, or to adjust the therapy program in response. Such data may also be processed in the therapeutic wellness device or external computing unit and combined with other, pre-existing information to give the user more complex, higher-level physiological program options or recommendations regarding adjustments to be made or therapeutic strategies to be pursued. Such data may be retained and manipulated over time, for example to provide ongoing metrics for changes or improvements in user physiology or performance, or for use with other wellness or exercise devices.

The use of galvanic skin response or neural activity sensors allows the therapeutic wellness device, alone or in conjunction with the external computing unit, to obtain data on a user's physiological state of relaxation and take action in response to that physiological state, in a process sometimes known as "biofeedback." This permits a user to command the therapeutic wellness device to produce or attempt to produce a generalized state or level of relaxation rather than a specific therapy activity or sequence. Once commanded to seek such a relaxation state or level, the therapeutic wellness device may attempt various therapy activities or strategies and measure the results in terms of relaxation state based on galvanic skin response or brainwave activity. Those activities or strategies that promote or tend to approach the desired relaxation state or level are then continued, while those which do not are abandoned. The resulting activities or strategies from this feedback process may then be retained and used for, and also refined during, future relaxation sessions.

The increased control and sensor feedback also promotes more subtle control for medical and physiological uses of therapy devices other than for focused, short-session active therapy or massage. For example, the mechanisms already present in many models of massage device can, under proper control and enhanced by sensor feedback, be used for longer periods, including overnight, in modes involving body soothing and therapy rather than active massaging.

As one example of a longer-session therapeutic use, persons suffering from gastroesophageal reflux disease, or GERD, often cannot comfortably sleep in a horizontal position. These GERD sufferers will often prefer to sleep in a semi-reclined position to avoid the potential for esophageal reflux. Many massage chairs feature power-driven reclining mechanisms permitting various angles of body recline, including angles suitable for use by GERD sufferers for sleeping. While active massaging may not be preferred for inducing or maintaining sleep, many of these chairs can deliver more attenuated and gentle massage suitable for longer-term soothing use and other benefits such as heat for soothing a user to sleep. A comprehensive control system in accordance with the present invention permits these features to be used with additional benefits to GERD sufferers. Not all GERD sufferers must sleep all night in a semi-reclined position; some are prone to esophageal reflux during only a portion of the night, usually the earlier portion, especially if they have consumed a large amount of food or beverage shortly before bedtime. These sufferers may prefer not to sleep in a semi-reclined position longer than necessary, past the time when the factors threatening esophageal reflux have passed. An embodiment of the present invention can provide a deeper recline toward full horizontal later during the night once the reflux symptoms or threat have subsided, without requiring the sleeping user to wake to make the change in recline angle. This can be achieved by a timer activated by the user, or by sensor input detecting biometric factors such as stomach distension or breath acidity (pH).

Figure 9:
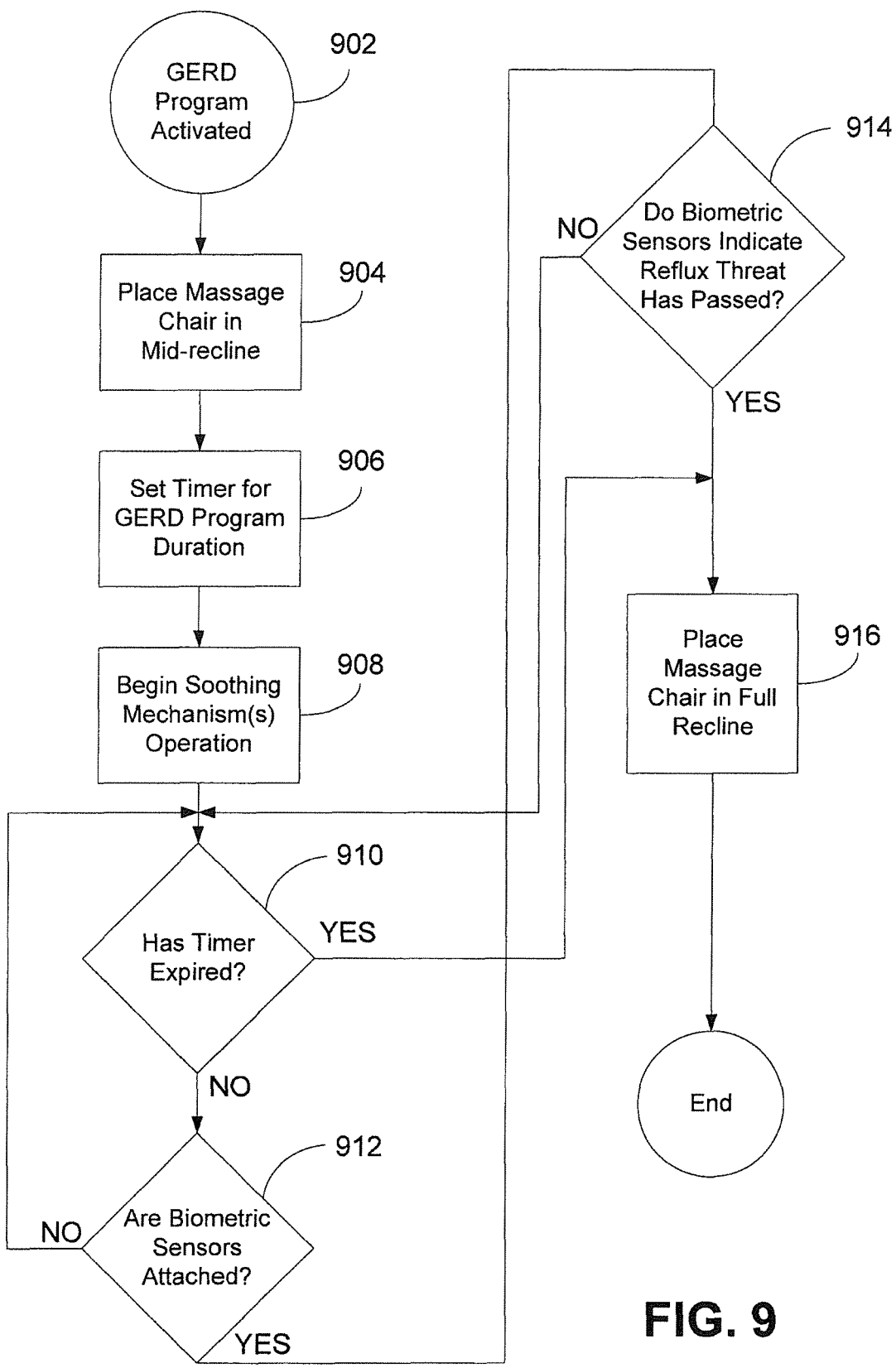
FIG. 9 is a flowchart of the operation of a particular massage chair soothing program for GERD sufferers.

One embodiment featuring a process for such an overnight soothing mode for a GERD sufferer is shown in FIG. 9. Upon activating (902) the program, the massage chair is placed (904) in a mid-recline position, and a timer is set (906) for the length of the program, and the operation of the selected soothing mechanisms begins (908). Until the program duration timer expires, and if biometric sensors are attached (910), the program continues until the sensors indicate (914) the reflux threat has passed. Upon termination of the program either through time expiration or biometric sensors indicating the threat has passed, the massage chair is placed (916) in full recline for the rest of the night.

Similarly, sensors can detect physiological problems indicating swelling or poor circulation in the feet that can be remedied by raising or lowering the user's feet relative to the heart or by stopping, starting, or altering the operation of a foot or calf massager on the massage device or in an ancillary device. Such indications may include skin temperature, pulse, and mass or size of the ankle. Moreover, real time sensor detection of conditions indicative of arthritis flareup or simply hypothermic conditions as during sleep can trigger the control system to attempt to alleviate these conditions by activating the heating mechanisms commonly found in therapy devices, as well as more advanced in-device heating systems involving minerals, or the heating mechanisms available in an ancillary appliance such as a heating pad or heated blanket, illustrated as item 144 in FIG. 1. More severe physiological reactions such as abnormal loss of consciousness or heartbeat irregularities can also be detected by these sensors, and the therapy, recline, or soothing program can altered or terminated in response.

The use of a therapeutic wellness device in medical applications or for longer periods with less healthy users presents additional opportunities to provide additional user benefits. For instance, long periods of constant sitting or lying without moving can lead to pressure-induced skin ulcers, also called bedsores. The risk of such ulcers can be reduced by periodically adjusting or redistributing the patient's weight onto different parts of the surface on which the patient is sitting or lying. The patient can do this manually by shifting body weight, and the therapy device sensors described above can feed real-time body pressure information to the control system, which can then advise the therapy device user when and how to perform such weight shifting or redistribution. Alternatively, this weight redistribution may be performed by reconfiguration or shifting of the sitting or lying surface itself, as discussed for example in U.S. Pat. No. 4,947,500 to Seiler. Many therapy devices comprise massage or movement mechanisms that can fully or partially accomplish such weight redistribution, generally through operation at a slower speed or more restricted travel than that normally used for active therapy. The control system in accordance with an embodiment of the present invention may be programmed to receive such sensor data and, in response, automatically command the therapy device to perform the appropriate weight redistribution at appropriate times and intervals.

The use of therapeutic wellness devices for institutional, therapeutic, or medical applications and the handling of data in these contexts may implicate medical information confidentiality regulations. Accordingly, one embodiment of the present invention includes data security measures to protect user information, such as password protection, in the system software and on the computing unit or therapeutic wellness device itself.

Features of Software Applications Compatible with an External Computing Device

Exemplary embodiments of the present invention typically include software in the external computing unit that controls how that unit interacts with and controls the therapeutic wellness device. Such software may take any number of forms, from dedicated special-purpose industrial software loaded into hardwired processors to generalized, consumer-oriented applications native to particular wired or wireless device which may not only control the therapeutic wellness device but integrate the therapeutic wellness device into a broader range of lifestyle devices. Many wireless computing and communication devices provide a computing platform that allows for development of independent compatible applications that take advantage of the beneficial features of such devices, such as portability, Bluetooth or other communications link capability, display, input touch screen, and miscellaneous input or data gathering features such as an accelerometer and GPS receiver. An application running on such a device can use the device's communication link to connect the device to a therapeutic wellness device and achieve many of the functionalities and benefits described herein.

Although such an application works with and may be mostly directed toward a therapeutic wellness device, because the application may be used with a portable computing device or a computing device in a location remote from the therapeutic wellness device, the running application need not at all times be in communication with the therapeutic wellness device, or any particular therapeutic wellness device, in order to be useful. The application may instead independently maintain information that does not require the therapeutic wellness device to be present, and may pertain to other items beside the therapeutic wellness device. When a therapeutic wellness device is not present, the application may for example enter a demonstration mode where the capabilities of the therapeutic wellness device, the application itself, or both are previewed. Alternatively, in that situation the application may interact with the user in relation to matters other than those pertaining to an absent therapeutic wellness device, or to prepare the user for future use and interaction with an absent therapeutic wellness device once a therapeutic wellness device is again present. It may also assist the user in seeking out an appropriate therapeutic wellness device with which the application may interact.

An application running on a portable external computing unit typically will present the user with many screens of information and device control and command options relevant to the therapeutic wellness device. These screens may use any and all of the items of display, information, interaction, and control known to those of skill in the relevant computing art; for example, these screens may contain text, graphical figures and displays, and items for interaction and control such as buttons, selection lists, and data entry fields. Each screen may have certain common features, such as a title bar and certain navigation selections. Using the navigation selections, the user may choose to go back to the previously displayed screen, go to a list or menu, or go directly to a home screen. The items described herein as "screens" need not be full-display screens, but may also take the form of dialog boxes, pop-ups, or other items appearing on top of a screen or taking up only part of the total display space.

The screens in an application need not be static or generic, but may be customized to a particular user and be context sensitive. They may also be upgraded, replaced or substituted, permanently or temporarily, by alternate screens from an external source, either at user request or automatically. For example, the manufacturer or distributor of the therapy product or of the application, or a third-party provider, may make available, on a website or by other means, or automatically distribute application version updates or upgrades, or may temporarily make available, on a website or by other means, or automatically distribute seasonal, holiday-themed, or event-driven screens. The overall appearances, color schemes, or themes of the screens may also be changed automatically or at user command as a "skins" change.

The types of screens presented by the application and the types of interaction with and control exercised over a therapeutic wellness device may depend on the type or model of therapeutic wellness device being interacted with and controlled from the application. Accordingly, in one embodiment of the present invention the application obtains type or model information about a particular therapeutic wellness device with which the application may be called upon to interact, either directly from the therapeutic wellness device itself or from an information listing about that therapeutic wellness device, the information listing being found on a data network such as the Internet. Using that information, the application may adjust itself to work with that particular type or mode of therapeutic wellness device, both in the application's user interface and in the application's control scheme. For instance, if a particular type or mode of therapeutic wellness device does not support a particular therapy feature that the application would otherwise present to the user, the application can indicate the feature is unavailable, for example by "graying" it or hiding it, or the application can translate the commands or issue alternate commands that implement the closest available feature supported by the therapeutic wellness device.

As well as adapting itself to the type or model of therapeutic wellness device to which the external computing unit running the application is connected, the application may also adapt itself to the type or model of external computing unit itself. Different hardware devices feature different input and screen functionalities, for example, and the application may compensate for, adjust to, or take advantage of differences in hardware capabilities and usage. For example, when running on a multi-user external computing unit, the application may add a screen to provide for identification of the user. An application running on hardware having a larger display may include more information and graphics on each screen it presents. An application running on hardware that does not include a touch screen may offer alternate ways while using only the input devices included with that hardware to permit a user to produce an input that is equivalent to or simulates a pinch or other finger gesture. An application running on a hardware unit that does not have sufficient computing power or computing resources to accomplish certain high-performance features may, when called up to engage in such a high-performance feature, instead engage in a similar, lower-performance feature, such as displaying sequential still pictures instead of full motion video.

The application may obtain and maintain data pertaining to the user that goes beyond the therapeutic wellness device or a particular session with that device. Such data may comprise, for example, the user's weight. The user's weight may be obtained directly from sensors in the therapeutic wellness device, if the sensors are capable of rendering usably accurate absolute weight. Alternatively, if the sensors in the therapeutic wellness device are capable of rendering only usably accurate relative weight over a limited range of weight, the user may be asked, in order to calibrate the relative weight sensors, to enter his or her weight while sitting in a massage chair or placing the user's body on a therapeutic wellness device; in future sessions with that therapeutic wellness device, the difference in weight with relation to the original calibrated weight can be used to calculate the user's new weight. Such data may also comprise patterns or schedules of therapy sessions, based on explicit input from the user or from the user's past patterns of therapeutic wellness device use. If, for example, the user has established a pattern of using the therapeutic wellness device in a certain way at a certain time of day, or if the user has asked to be reminded at that time of day, the application may issue a reminder to the user if that time of day passes without the user having activated the therapeutic wellness device. Such data may also comprise subjective, self-reported user data such as mood score. As with physiological data, such subjective data once collected, assembled into trends, and otherwise manipulated may be useful for reporting user progress and for suggesting various types of therapy based on the user's mood or change in mood.

Higher-Level Heuristics Undertaken by External Computing Unit and/or Therapeutic Wellness Device In one embodiment of the present invention, the application running on the external computing device interacts with the user on a very high, holistic, physiological level rather than involving the user in specific matters directly pertaining to the mode of therapy or operation of the therapeutic wellness device. In this embodiment, the application may make such high-level inquiries of the user as, "How do you feel?" and "How do you want to feel?" and then apply diagnostic heuristics to translate the user's high-level physiological answers into specific massage and wellness strategies, modalities and procedures. Feedback heuristics may also be brought to bear, with the application inquiring of a user, "Did this [or a previous] therapy session satisfy your needs?" or "What more or different relief would you like to experience?" and use the correlation or difference between the therapeutic strategy previously applied and the results obtained to engage further or different therapeutic strategies.

These heuristics may comprise manifold internal translations and calculations from physiological states and user preferences into therapeutic wellness device mechanics. For example, there exists a positive correlation between massage chair recline angle and massage intensity, because as recline angle increases, gravity brings a user's back down more squarely and forcefully on the massage elements. Because of this, there are certain maximal intensities of chair-based massage that can only be delivered in a more fully reclined position. Accordingly, when the user's input leads an application running on an external computing unit, other computing resource, and/or a massage chair to "decide" that a very strong massage is called for, the user can be instructed to recline the massage chair or the massage chair can be automatically reclined. In situations where a manual adjustment may be necessary, such as removing pillows or padding in order to obtain a stronger massage, the application can inform the user of the steps to take. The heuristic intelligence of this and similar embodiments of the present invention permits the system to keep track of such physiological to mechanical translations and special knowledge rather than requiring the user to do so.

Figure 16:
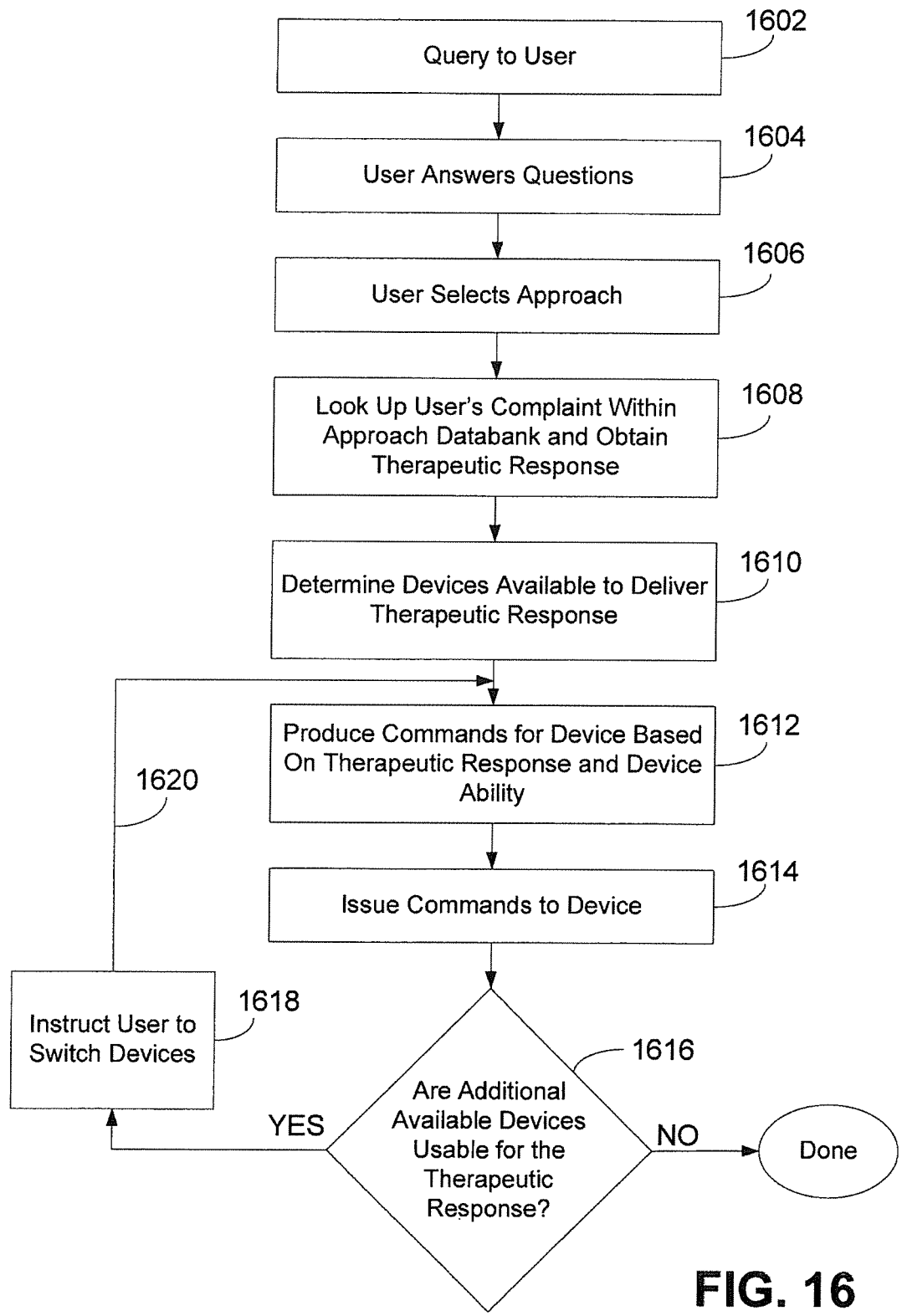
FIG. 16 is a flow diagram showing construction of a therapeutic response for implementation by a wellness device in response to a user's answers to high-level questions.

In one embodiment, as depicted in FIG. 16, the application queries (1602) the user with one or more high-level questions such as, "how do you feel?" "where does it hurt?" or "is the pain sharp or dull?" The user responds (1604) with appropriate answers, such as by entering text or selecting an answer from multiple choices. The application responds therapeutically to the user's indicated condition or complaint, but it need not do so according to just a single approach. A user may have assembled several different approaches to one or more conditions or complaints, for example, one approach obtained from the user's medical provider, one approach obtained from a massage or therapy expert, which the user may obtain from the professional's blog or from the manufacturer of the therapeutic wellness device, and one approach created by the user or another user. Each of these approaches comprises a databank of various complaints and conditions and the corresponding therapeutic response to be used to answer each. The user may select (1606) which of these approach databanks the application is to use in addressing the user's complaints.

The application uses the selected approach to convert (1608) the user's complaint into a therapeutic response. Such conversion may be accomplished for example through a lookup table, programmed formula, or decision tree. Such therapeutic response may consist of therapy steps, for example: (a) apply heat to the area for a particular time period; (b) follow with a vigorous pounding massage for a particular time period; (c) follow with a gentle kneading massage for a particular time period; (d) follow with more heat for a particular time period. The application determines (1610) which therapeutic wellness devices are available to the user, and combines the therapeutic response with the abilities of the available devices to produce (1612) a series of commands to a connected device. The conversion to instructions may be achieved for example through a lookup table or programmed formula. The application then issues (1614) the commands to the device. If (1616) the therapeutic response requires more than one available therapeutic wellness device to be employed in sequence, when the first device has finished its operations, the application instructs (1618) the user to switch devices, and when the second device is in place, the application repeats (1620) the process of producing commands for that device and issuing those commands. This process repeats for as many therapeutic wellness devices are available. Where multiple devices can be employed on the body at once, the commands can be sent to the various employed devices simultaneously.

In another embodiment, the higher level heuristics are represented by an interactive graphical depiction with which the user interacts to indicate the user's general preference for location of therapy, without directly selecting the particular therapy operations in which the user desires the therapeutic wellness device to engage. In this embodiment, a user selects a portion of a graphical device such as a diagram of a human body or a diagram of the wellness device, to indicate where on the user's body therapy is desired or there is a problem or discomfort. Such selections can be made, for example, by finger touch or hand gesture. In connection with this, the diagram of the human body portion or of the therapy device may be coded with color or other graphical devices to assist the user in making selections. Where the full diagram is too large to fit comfortably in the display, the diagram may be scrolled, zoomed, or otherwise adjusted to assist in making a selection. In addition, gestures such as horizontal or vertical squeezing or spreading may be used to set the horizontal or vertical extent and span of the therapy; this can also be done during the therapy, with the user adjusting the width and height of therapy for maximum comfort.

Figure 17:
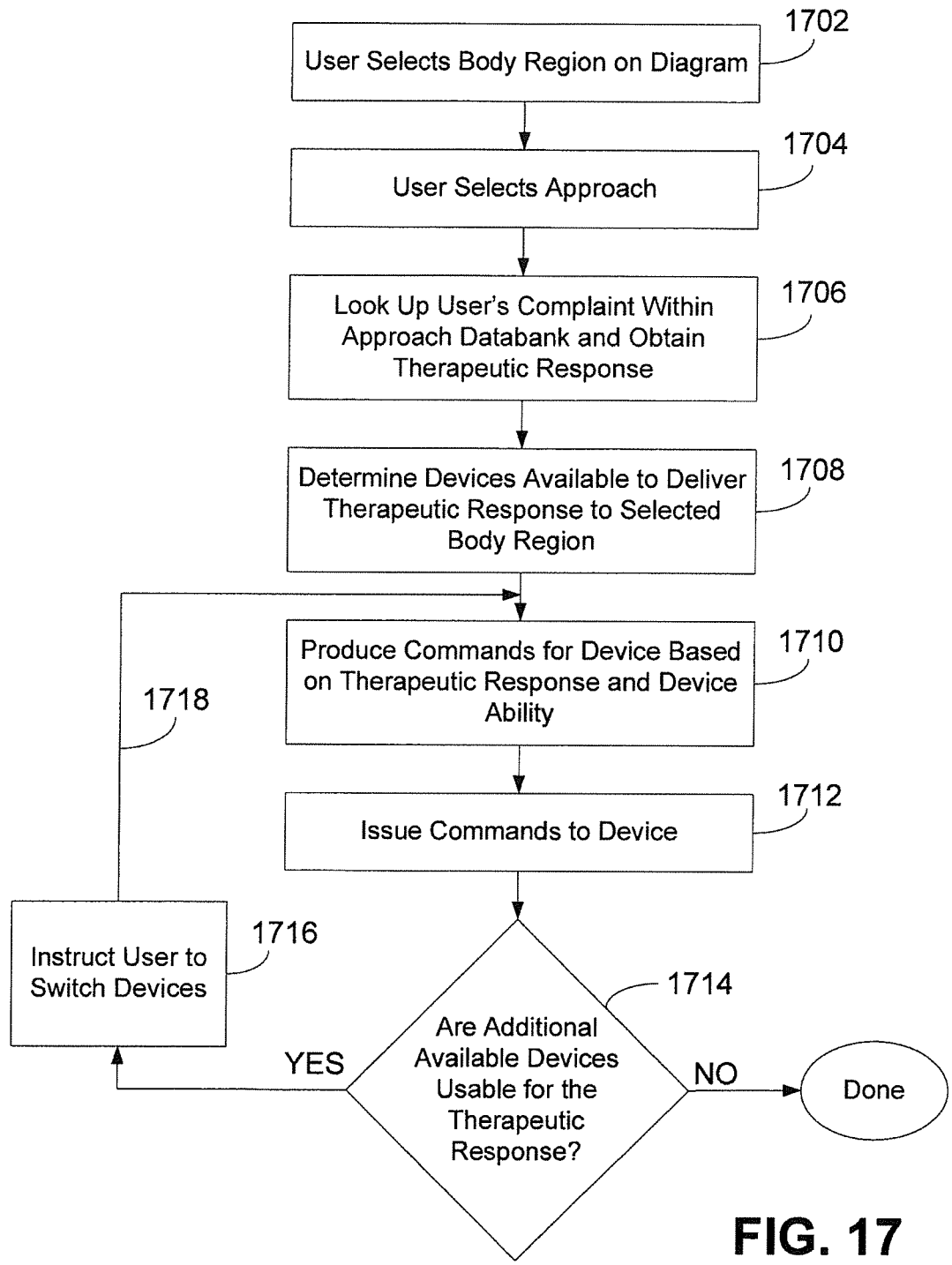
FIG. 17 is a flow diagram showing construction of a therapeutic response for implementation by a wellness device in response to a user's selection of a body region on an interactive diagram.
Figure 18A:
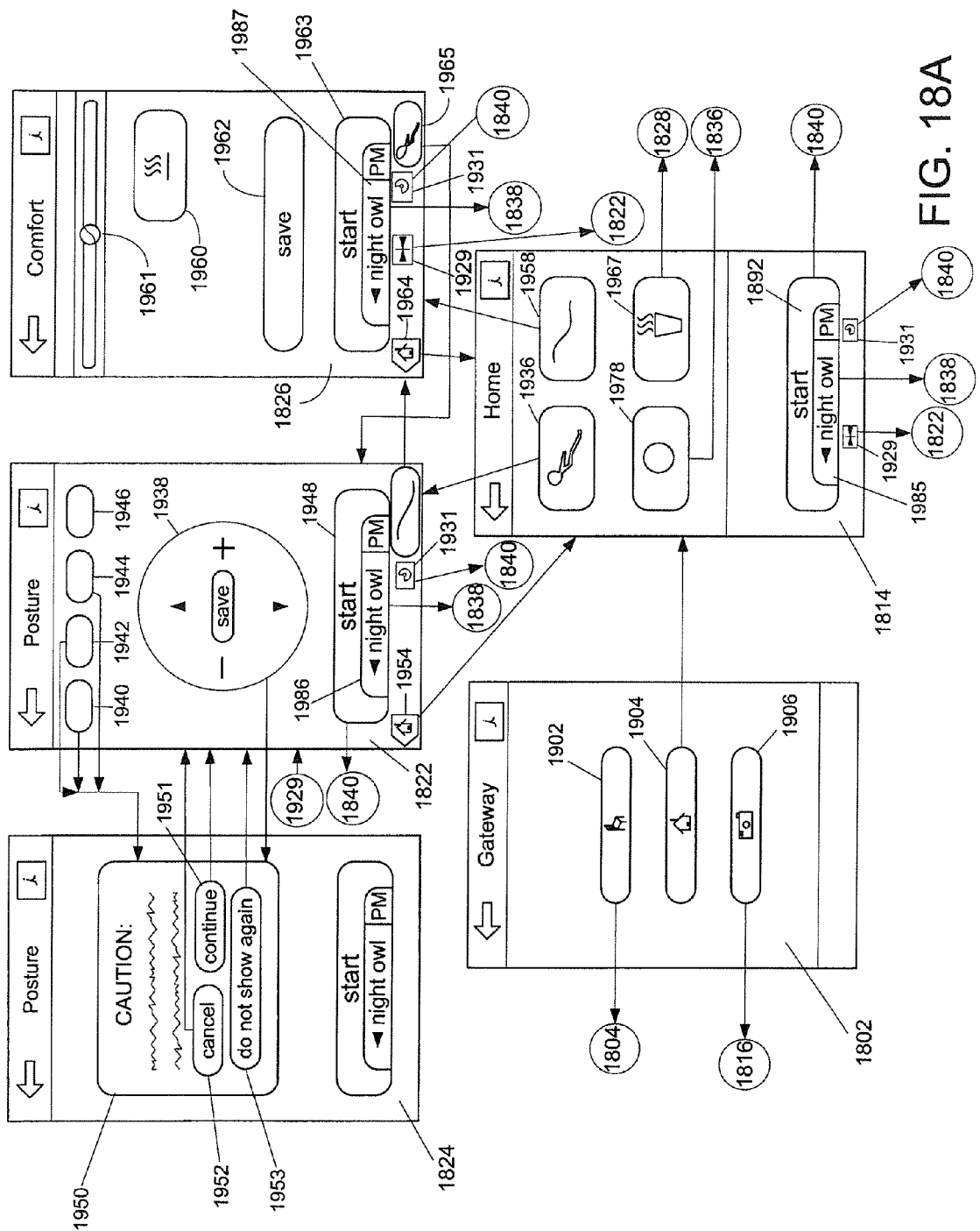
Figure 18B:
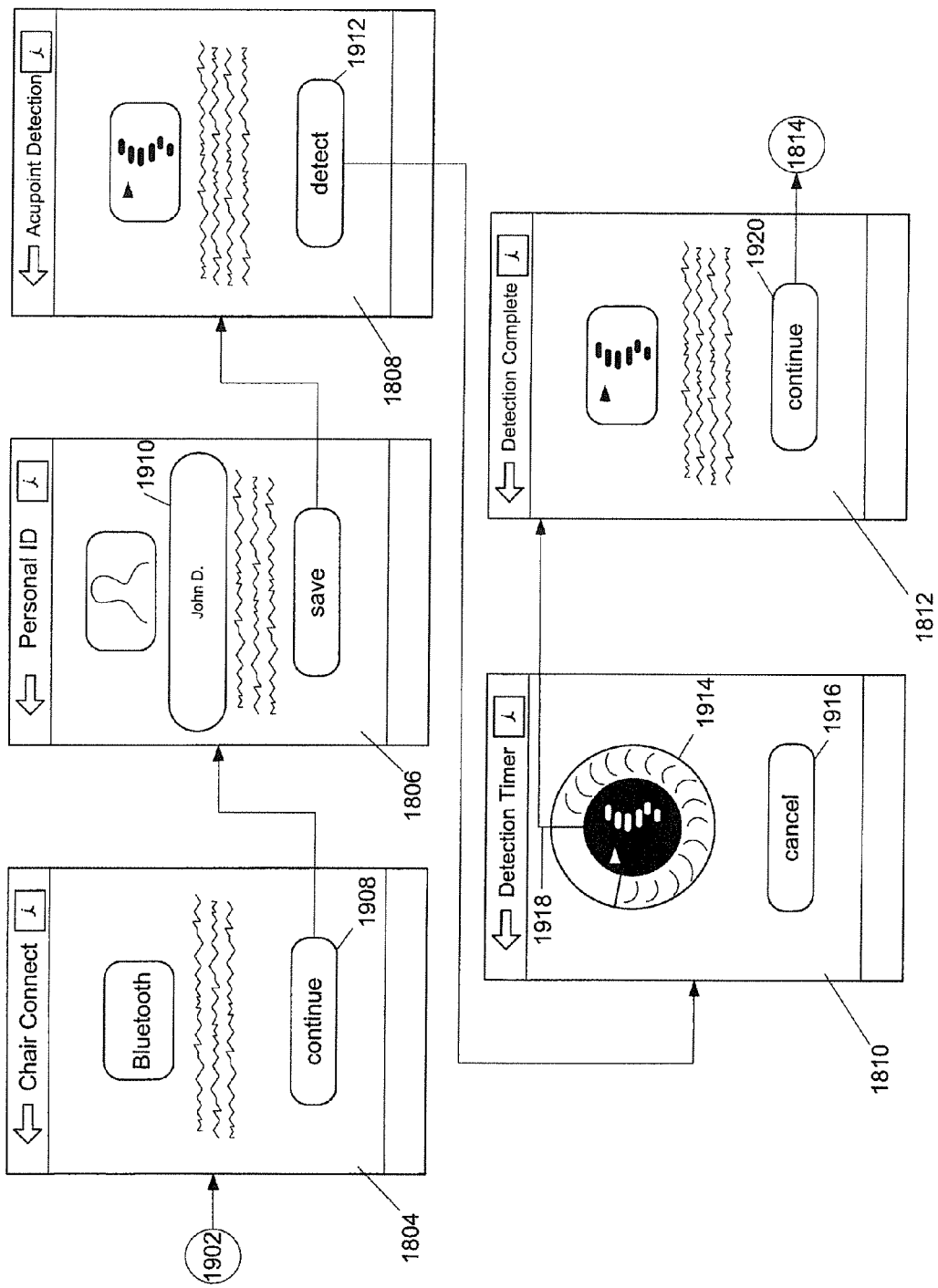
Figure 18C:
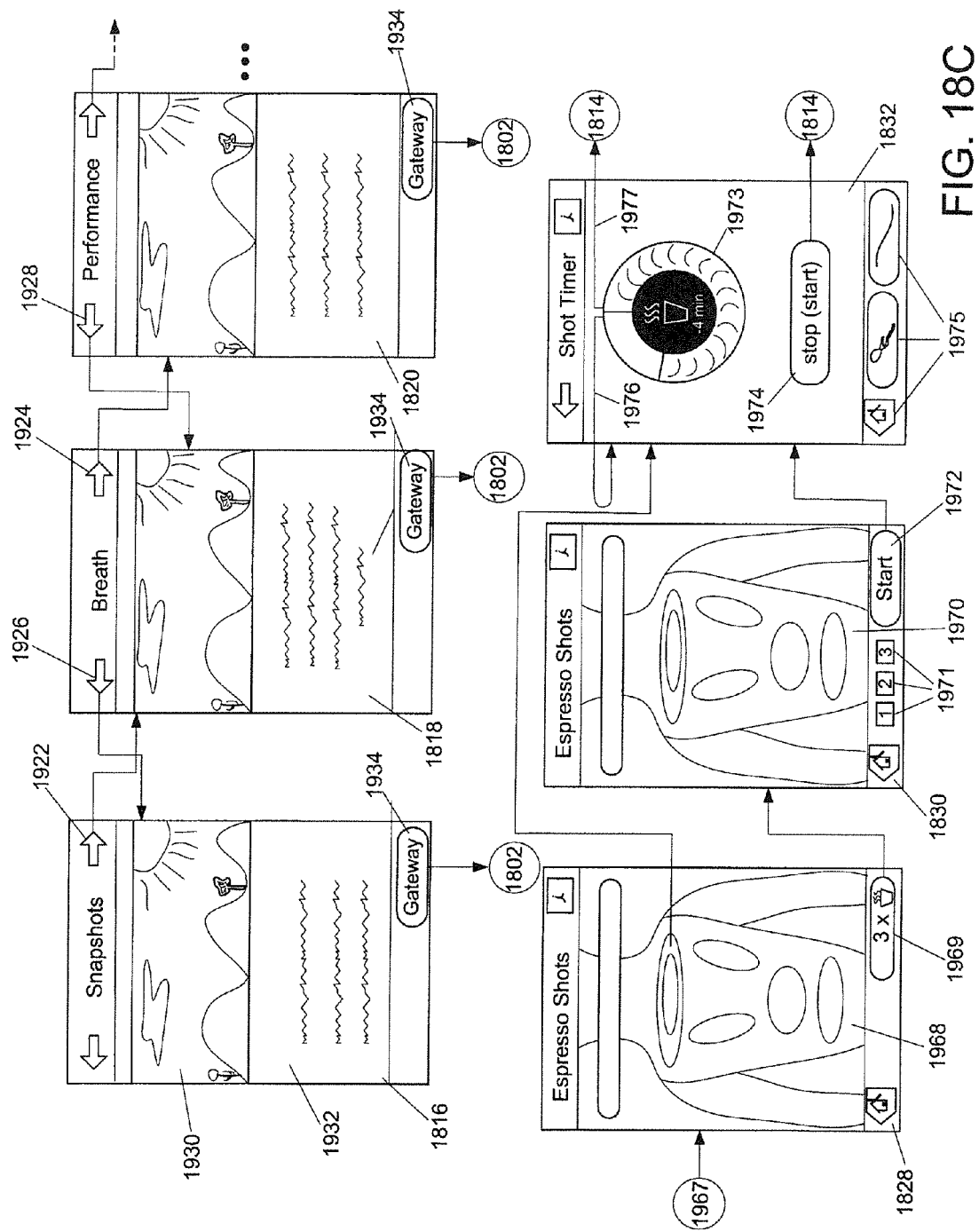

In an embodiment with a human body diagram, as depicted in FIG. 17, the user selects (1702) the portion of the body diagram to indicate the body region for therapy. The application responds therapeutically to the user's indicated condition or complaint, but as with the heuristic questioning embodiment, the application need not do so according to just a single approach. A user may have assembled several different approaches to body region therapy, for example, one approach obtained from the user's medical provider, one approach obtained from a massage or therapy expert, which the user may obtain from the professional's blog or from the manufacturer of the therapeutic wellness device, and one approach created by the user or another user. Each of these approaches comprises a databank of various body regions and the corresponding therapeutic response to be used to answer each. The user may select (1704) which of these approach databanks the application is to use in addressing the user's complaints.

The application uses the selected approach to convert (1706) the user's selected body region into a therapeutic response. Such conversion may be accomplished for example through a lookup table, programmed formula, or decision tree. Such therapeutic response may consist of therapy steps, for example: (a) apply heat to the area for a particular time period; (b) follow with a vigorous pounding massage for a particular time period; (c) follow with a gentle kneading massage for a particular time period; (d) follow with more heat for a particular time period. The application determines (1708) which therapeutic wellness devices are available to the user, and combines the therapeutic response with the abilities of the available devices to produce (1710) a series of commands to a connected device. The conversion to instructions may be achieved for example through a lookup table or programmed formula. The application then issues (1712) the commands to the device directed to the selected body region. If (1714) the therapeutic response requires more than one available therapeutic wellness device to be employed in sequence, when the first device has finished its operations, the application instructs (1716) the user to switch devices, and when the second device is in place, the application repeats (1718) the process of producing commands for that device and issuing those commands. This process repeats for as many therapeutic wellness devices are available. Where multiple devices can be employed on the selected body region at once, the commands can be sent to the various employed devices simultaneously.

Processing of Ancillary and Non-Therapy Data and Commands

The application need not wait on user input for navigation through its various screens, but may feature a demonstration mode that demonstrates its screens, features and abilities, the features and abilities of the therapeutic wellness device, or both. Such a demonstration mode may take the form of an interactive or guided tour of various features, with or without user input directing or interacting with it. This demonstration mode may operate with or without a therapeutic wellness device being present. With one or more therapeutic wellness devices present, it may put the device or devices through such publicly visible actions or sequences as may tend to attract the attention of passers by or the public in a retail space.

One aspect of wellness balance involves personal rhythm and schedule, and accordingly the functionality of the therapeutic wellness device and/or the external computing unit may involve temporal data, such as time of day, day of the week or month, or season. One form of temporal functionality may involve scheduling of therapy sessions. Any of the external computing unit, the therapeutic wellness device, or a connected ancillary device may issue an alarm signal such as a tone or light tone at a preset time requested by the user, especially a time when the user desires a therapy session to begin. This may be especially useful for keeping the user on a regular schedule by calling to the user to begin a pre-sleep bedtime therapy session, such as massage.

Such time-based notification may move beyond a simple "alarm clock" function into the area of motivational incentivization, for example encouraging the user to keep to a preset schedule of massage or other therapeutic activities. The can be achieved for example by continuing to issue the alarm tone until the user begins the therapy session or other wellness activity. Time of day or other temporal information may be used to influence the selection of the type of therapy to be performed. This may be used to construct a day-long to season-long course of time- and context-sensitive therapy, taking into account the different types of therapy that may be most appropriate for periods such as morning, midday, post-workday, evening, and pre-sleep. The user may also schedule a therapy session to begin automatically if the user is already in contact with the therapeutic wellness device, for example if the user is already sitting in a massage chair or spends time in a massage chair for other purposes, using such chair as an office chair or sitting chair. As another example, a user who sleeps in a massage chair may program a massage or other stimulation to wake the user by automatically beginning at a time either preset by the user or based on the times of the user's previous uses of waking functions.

Beyond time-based notification, other types of information may be set to trigger notification to the user or interaction with or modification to the therapy program. For instance, the user may instruct the system to notify the user or modify or terminate the therapy session if an E-mail, web-based, or other notification is presented to the external computing unit, or if a particular type of such notification is presented. Beyond this the external computing unit, by itself or in conjunction with other computing resources, may be set upon tasks such as information gathering and/or analysis instructed to take appropriate action such as user notification or therapy session termination if and when a particular item or type of information is gathered or when other types of computing projects are completed or reach a certain milestone or type of result.

Publicly available therapeutic wellness devices, such as those at airports, shopping centers, or other public facilities, may make their presence and location available to an application running on a portable computing device, either directly by wireless connection or by a listing on a data network such as the Internet. The portable device may determine its own location, for instance through direct data input from the user or from GPS data, and use that location and the locations of the available therapeutic wellness devices to alert the user to nearby available therapeutic wellness devices. In addition to locating nearby therapeutic wellness devices that are available for public use, the application may also locate nearby therapeutic wellness devices that are being publicly demonstrated or that are available for sale, for example at nearby retail stores. Conversely, retail exhibition or activity pertaining to therapeutic wellness devices or external computing units that is being held at a particular location may be able to connect with and advertise itself to all therapeutic wellness devices and/or external computing units which have reported their current geographical positions as being within a certain distance from the retail event.

Exemplary Flows and GUI Screens for a Software Application on an External Computing Unit Charts and flow diagrams of graphical user interface screens from an external computing unit software application controlling a therapeutic wellness device are illustrated in FIGS. 18A through 18D. In one embodiment of the present invention, upon being invoked the application typically presents the user with an opening or "gateway" screen 1802. This screen presents the user with an option button 1902 to set up the application and the therapeutic wellness device, either if this is the first time the user has used the application and/or the therapeutic wellness device, or if the user desires to change the current settings of the application and/or the therapeutic wellness device. This screen also presents the user with a button 1904 to move to a "home" screen and a button 1906 to move to certain informational screens.

Upon selecting the set-up option button 1902 from a gateway screen or from any other screen, the user may be presented with a set-up screen or screens that permit the execution of various initialization routines, which may take place sequentially, one after another. One such routine involves setting up the communication link between the therapeutic wellness device and the external computing unit. The specific technical steps to be pursued in order to set up the communications link vary depending on the type of link to be established, but are known to those of skill in the relevant data communications art. The screens to be shown in connection with establishing the link also vary depending on the link type. In one embodiment, in setting up a Bluetooth communications link, the user may be shown a screen 1804 that instructs a user on the steps to take with the "settings" functionality of the user's portable communication or computing device running the application in order to establish a Bluetooth pairing with a Bluetooth-enabled therapeutic wellness device. Since the Bluetooth pairing may be established outside the application, there need be no interactive items or controls on the link establishment screen other than a button 1908 to continue past this step, but alternatively the link may be established by the application itself, in which case the link establishment screen may feature such control, display and interactive items as are necessary to establish and configure the link. If multiple communications links are available, one step of the routine and one or more screens may be devoted to selecting which link or links to set up.

Beyond establishing the link, another initialization routine involves identifying the user to the application. In one embodiment, upon indicating the user is ready to continue past the linking step by selecting button 1908, the user is taken to a user identification screen 1806. Identification of the user to the application may be as simple as setting a personal user name or ID in field 1910, or may involve gathering or entering additional user-based information such as a password or security biometrics such as a fingerprint or retinal scan, and the user's sex, age, weight, or other health parameters. The quantity and type of interactive items on the user identification screen or screens depend on the amount and type of user information to be entered. The gathered or entered information is stored by the application and/or the therapeutic wellness device and is retained between therapy sessions and/or application sessions; it may be used for instance to guide therapy sessions or in the application display to label the user preset buttons with the user's name or ID.

In one embodiment, upon saving personal identification information by selecting button 1910, the user is taken to another initialization routine screen 1808. This routine involves detection of the size and significant points in the portion of the user's body to be addressed by the therapeutic wellness device, for example detecting the size of and/or massage points in the user's back in connection with use of a massage chair. Various techniques for performing this detection are known to those of skill in the relevant massage device art. Upon initiating the detection process by selecting button 1912, the user is taken to a detection process screen 1810. This screen may be as simple as an elapsed time indicator 1914 for alerting the user how much more time is required for the detection step, and a cancel button 1916 for aborting the detection step. When the timer elapses 1918, the user may be taken to a screen 1812 announcing that the detection is complete. Depending on the communications link, the application, and the type of therapeutic wellness device, completing other initialization routines may be required or advisable as well. Once all the initialization routines are complete, the user is returned to a main screen. In one embodiment, selecting continue button 1920 on screen 1812 takes the user to home screen 1814. The data collected by the initialization routines are retained for future use, and once these routines have been run the gateway screen may be bypassed, so that upon starting up the application the user may be taken directly to a home screen. However, the initialization routines may at any time be revisited to set new values or reconfigure the application, therapeutic wellness device, and communications link.

Not all the screens of the application need pertain directly to control of or interaction with the therapeutic wellness device. Another mode of operation may involve a series of therapy-device-independent informational screens that may be used to impart general health, fitness, wellness, and lifestyle information to the user, here called "snapshots." In one embodiment, selecting button 1906 on gateway screen 1802 takes the user to an introductory screen 1816 that explains the purpose of the informational screens. Selecting the forward movement button 1922 on that introductory screen takes the user to the first informational screen 1818. Selecting the forward movement button 1924 on that screen takes the user to the second informational screen 1820. The user may continue sequencing through the other informational screens in this way, or move backward through them by selecting the backward movement button, such as 1926 or 1928. Each of these screens may take the form of a text-and-image based slideshow, with illustration 1930 and text 1932, and may have added audio or video. The amount of information to be imparted may be large enough to require several long screens, and each such screen may have standard navigation items and buttons to permit the user to move through the full extent of each screen, and in addition to navigate from screen to screen forwards or backwards, to jump or return directly to any particular screen. For example, selecting gateway jump button 1934 on each page moves directly from any screen back to the gateway screen 1802. The user may also be given the option, if the user has previously perused only a portion of the message screen set, to navigate directly in a subsequent session to the point in the slideshow where the user last left off. These screens may be static, or they may be dynamically updated by the therapeutic wellness device manufacturer, the application manufacturer, or third-party providers, at the user's request or automatically.

A home screen 1814 can be reached by selecting button 1904 from the gateway screen. The home screen may serve as the main base screen in the application for controlling and interacting with the therapeutic wellness device. The home screen, as with any other screen in the application, need not be static but may dynamically change its features depending on the user's selections. The home screen typically may offer the user different modes and options as well as "quick start" options that set the therapeutic wellness device into operation quickly.

When used in conjunction with a therapeutic wellness device such as a massage chair in which the user sits, one item selectable by the user from the home screen or from other screens may be a posture setting option. In one embodiment, selecting button 1936 from the home screen takes the user to "posture" screen 1822. Such a posture screen may include features such as a posture adjustment click-wheel-style control 1938 which through directional buttons can adjust the back rest or overall recline of a massage chair or massage table, as well as lift or lower a leg support. A posture screen may also feature present posture setting buttons such as 1940, 1942, and 1944 that bring all the support platforms of a massage chair or a massage table to a certain preset position, such as a stretching recline, a comfort or relaxing recline, a position optimal for viewing television, a fully upright position, or a preset position that the user prefers. Pressing button 1946 stores the current position of the therapy device as the user's preferred posture position. A posture screen may further feature a button 1948 to begin immediately a preprogrammed or automatically selected therapy program. The posture screen may also be reached by pressing a "restore" button 1929 found on various screens, which button also brings the backrest of a controlled massage chair to a full upright position.

Certain selections on the posture screen have the ability to cause movement or change in configuration of the therapeutic wellness device in a major way that may startle or injure the user or a bystander. Accordingly, a warning screen 1824 appears whenever the user selects a feature, button, or command such as 1940, 1942, and 1944, that does or may involve such a movement, A dialog box 1950 may pop up on the external computing unit screen to caution the user that the chair is about to move automatically. An alternative warning that does not depend on the user viewing the external computing unit's screen may also be used for this safety function, such as a noise, tone, or light, originating either from the external computing unit, the therapeutic wellness device, or an ancillary device connected to or in communication with the external computing unit or the therapeutic wellness device. The dialog box may give the user the option to select button 1951 to continue with the move option, or to select button 1952 to cancel it. The dialog box may also give the user the option to select button 1953 to accept all future moves and not to be shown the dialog box again. The fact of the user's selecting this option, along with circumstances such as the date and time this choice was made, can be recorded or even transmitted to other locations, both for reference by the system so as not to show the dialog box again, and also for liability avoidance purposes. Once selected, this no-warning mode can be cleared by the user at a later time.

Posture screen 1822 may also have standard navigation buttons, which may include a button 1954 to take the user directly to the home screen and a button 1956 to take the user directly to a "comfort" screen 1826. Since this option and screen involve parameters that may be effectively changed during a therapy or massage sequence, this screen may be accessed during a therapy or massage operation as an interruption to or excursion from the screen or screens displayed during that operation, and the user may then be returned to the therapy or massage operation screen or screens when this option and screen are completed.

In one embodiment, selecting button 1958 on the home screen, or 1956 on the posture screen, or certain other selections on other screens, takes the user to a "comfort" screen 1826 featuring comfort setting options. Such a comfort screen may include features such as a button or control 1960 for selecting or adjusting heat to be delivered by the therapeutic wellness device or other sensory stimuli to be delivered by other ancillary devices such as aromatherapy or lighting devices. It may also feature a control 1961 for adjusting the amplitude of vibrations or of massage motions. It may further feature a preset button 1962 that stores or recalls the user's preferences for such comfort services. A comfort screen may further feature a button 1963 to begin immediately a preprogrammed or automatically selected therapy program. A comfort screen may also have standard navigation buttons, which may include a button 1964 to take the user directly to the home screen or a button 1965 to take the user to the posture screen. Since this option and screen involve parameters that may be effectively changed during a therapy sequence, this screen may be accessed during a therapy operation as an interruption to or excursion from the screen or screens displayed during that therapy operation, and the user may then be returned to the therapy operation screen or screens when this option and screen are completed.

Because the posture and comfort screens are ideally accessible as an interruption or temporary excursion from many different screens, it is advantageous to allow these screens to be accessible without taking up valuable screen "real estate" with items and controls on all those many other screens to initiate temporary transfer to these screens. This can be accomplished by a command issued other than through a screen control, and this can be achieved for example by using the navigation tilt, navigation slide, or navigation snap device manipulation command schemes disclosed herein.

Another item selectable by the user from the home screen 1814 or from other screens is a mode that permits the user to quickly and easily execute a custom therapy or massage action or assemble a custom therapy or massage session based on discrete massage components that can be mixed and matched. Selecting button 1967 on the home screen takes the user to a discrete therapy or massage program screen 1828, here called "espresso shots." The first screen 1828 allows the user to select a single therapy or massage activity by selecting a portion of the body that is ailing or to which the user desires attention. This selection scan be made from a graphical device such as a diagram of a human body 1968. Alternatively, a diagram of a therapeutic wellness device or other diagram may be used for selection of various locations to indicate various therapy or massage activities. Such selections can also be made by finger or hand gestures. In connection with this, the diagram of the human body portion or other diagrams may be coded with color or other graphical devices to assist the user in making selections. In addition, gestures such as horizontal or vertical squeezing or spreading may be used to set the horizontal or vertical extent and span of the therapy; this can also be done during the therapy, with the user adjusting the width and height of therapy for maximum comfort.

In one embodiment, selecting an area on the body diagram 1968 on the first espresso shots screen 1828 begins the therapy or massage activity associated with the selected area and takes the user to the timer screen 1832 for the duration of the therapy or massage activity. Selection of the sequence assembly button 1969 takes the user to a second espresso shots screen 1830, where the user may assemble a sequence of up to three therapy or massage activities. As the user selects one or more of the various areas on the diagram 1970, the 1, 2, and 3 indicators 1971 illuminate, indicating the selected therapy activities have been loaded. When the user has selected the desired number of "stacked" activities, start button 1972 is selected, taking the user to the timer screen 1832.

The timer screen features an elapsed time indicator 1973 for alerting the user how much time is left in the therapy or massage activity or stacked assembly of activities, a stop button 1974 for aborting the single therapy or massage activity or assembly of activities and returning to the home screen, and standard navigation buttons 1975 for moving to the home, posture or comfort screens during the therapy or massage activity. In one embodiment, the timer screen functions differently depending on whether a single activity has been selected in the first screen or a stack of activities have been assembled in the second screen. When the time expires 1976 for a single activity, the activity ceases but the timer screen remains active, the stop button 1974 becomes a start button, and the user may repeat the selected activity by pressing the start button. When the time expires 1977 for a stacked assembly of activities, the last activity ceases and the user is returned to the home screen.

Another item selectable by the user from the home screen 1814 or from other screens is a mode making available for the user's use a list and selection of information and therapy or massage programs assembled by experts in health and fitness. Selecting button 1978 takes the user to programs screen 1834 listing programs such as 1979, 1980, and 1981 composed by various third parties and experts. Upon selection of one of these entries, for example 1980, the user is taken to a particular program screen 1836 featuring a detailed discussion 1982 of the therapy or massage program corresponding to that entry, created by the selected third party or expert, along with suggestions for obtaining maximum benefits from the therapy program, and a link 1933 to other resources authored by the expert, such as a blog or web page. This screen also includes a button 1983 to start the expert's therapy program; upon selecting this button and beginning the therapy program, the user is taken to the program timer screen 1840. This screen further includes navigation buttons 1984 to move among the various program screens or to return to the program listing screen.

Another item selectable by the user from the home screen 1814 or from other screens is a mode making available to the user a list of daily therapy programs that have been assembled by the therapeutic wellness device manufacturer, the application manufacturer, third-party providers, and/or the user. Selecting display button 1985 on the home screen, which displays the currently proposed massage or therapy activity, or the similar display buttons 1986 on the posture screen and 1987 on the comfort screen takes the user to a daily program screen 1838. This screen features an abbreviated list 1988 of available programs, for example presented as a picker wheel, from which the user may select a particular program to associate it with the start button. The associated program is then associated with and displayed with the start buttons on other screens, such as 1948 on the posture screen and 1963 on the comfort screen, allowing the user to initiate the selected program quickly from any screen. The user may then select start button 1989 to begin the selected program. In one embodiment, each available programs are assigned to particular times of day and/or particular days of the week, and the application may use the current time of day to propose a particular program from the list, although the user is free to select any other program as well. In this embodiment, a program associated with the start program by the user may remain associated only during the period of the day to which it belongs. This screen also features a navigation button 1990 to take the user to the listing screen of programs 1834, and a reset button 1991 to clear a program the user has associated with the start button and resume the association with the start button of the program suggested by the application.

Upon pressing start button 1989, the user is taken to a program timer screen 1840, and the program is initiated. This screen is also reached, with the program being initiated, from start buttons 1992 on the home screen, 1948 on the posture screen, 1963 on the comfort screen, and 1983 on a particular third-party program selection screen such as 1836. This screen can also be reached without the program being initiated from navigation button 1931 on various screens. The timer screen in this embodiment features an elapsed time indicator 1993 for alerting the user how much time is left in the selected therapy or massage program. When the time elapses 1994, the user is taken back to the home screen 1814. This screen also features a stop button 1995 for aborting the selected program and returning the user to the home screen, and a program selector button 1996 to take the user back to the program selection screen to select another program. It also features standard navigation buttons 1997 for moving to the home, posture or comfort screens during the therapy or massage program.

In those screens featuring an indication of elapsed time in certain embodiments, the indicator is designed to provide an easily gauged graphical indication of the elapsed time and/or the time remaining in comparison to the total time period. The indicator also indicates the pertinent time numerically as well as graphically. It updates either continuously or in discrete implements as is most advantageous for the event being timed. In case of estimated time durations, it is not necessary for the timer to completely elapse before the preferred event expires, and as necessary or useful the user can be taken to the next screen before the timer has finished counting down. Preferably all time indicators in the application follow the same graphical format in order to present the user with a consistent and familiar signal that elapsed time is being indicated.

Navigation of Portable Computing Device Screens Through Manipulation of the Physical Device In certain embodiments of the present invention, certain manipulations of a portable computing device having an accelerometer or other position or velocity sensing apparatus can be used to navigate among screens or content on that computing device. This is useful for navigating among screens without having to commit display "real estate" to navigation buttons or other items. Although on computing devices having touch screens navigation may also be accomplished by finger gestures such as flicking, having a method of navigation alternative to finger gestures is useful when finger gestures are being captured by a particular screen for non-navigational purposes, such as for purposes of invoking certain types of therapy, as described elsewhere herein. While the embodiments described here are applicable to external computing units controlling therapeutic wellness devices, they are also equally applicable more generally anywhere a user seeks to navigate through screens of content while using a portable computing device.

In one embodiment, the user may navigate from one screen to the next by tilting the portable computing device, in what may be called a "navigational tilt". For example, if the user were viewing a first screen of data is at a particular position with respect to an axis normal to its screen, for example when the top of the device is at the uppermost angular position with respect to a screen-normal axis, when the device is rotated or tilted about the screen-normal axis by a particular number of degrees, the first screen may change or navigate to a second screen. If the number of degrees of tilt required for a screen change is set close to ninety, this would have the effect of a screen that is displayed when the device is in a "portrait" orientation transitioning to another screen when the device is tilted onto its side into the "landscape" orientation. However, any size of tilt angle may be specified for a navigational change. For example, if a forty-five degree navigation tilt were specified. A first screen showing when the device is in a portrait orientation would transition to a second screen and then to a third screen as the device is tilted onto its side into a landscape orientation. If a ten-degree navigation tilt were specified, as the device is tilted onto its side from portrait to landscape orientation, the device would navigate through eight additional screens.

Figure 13:
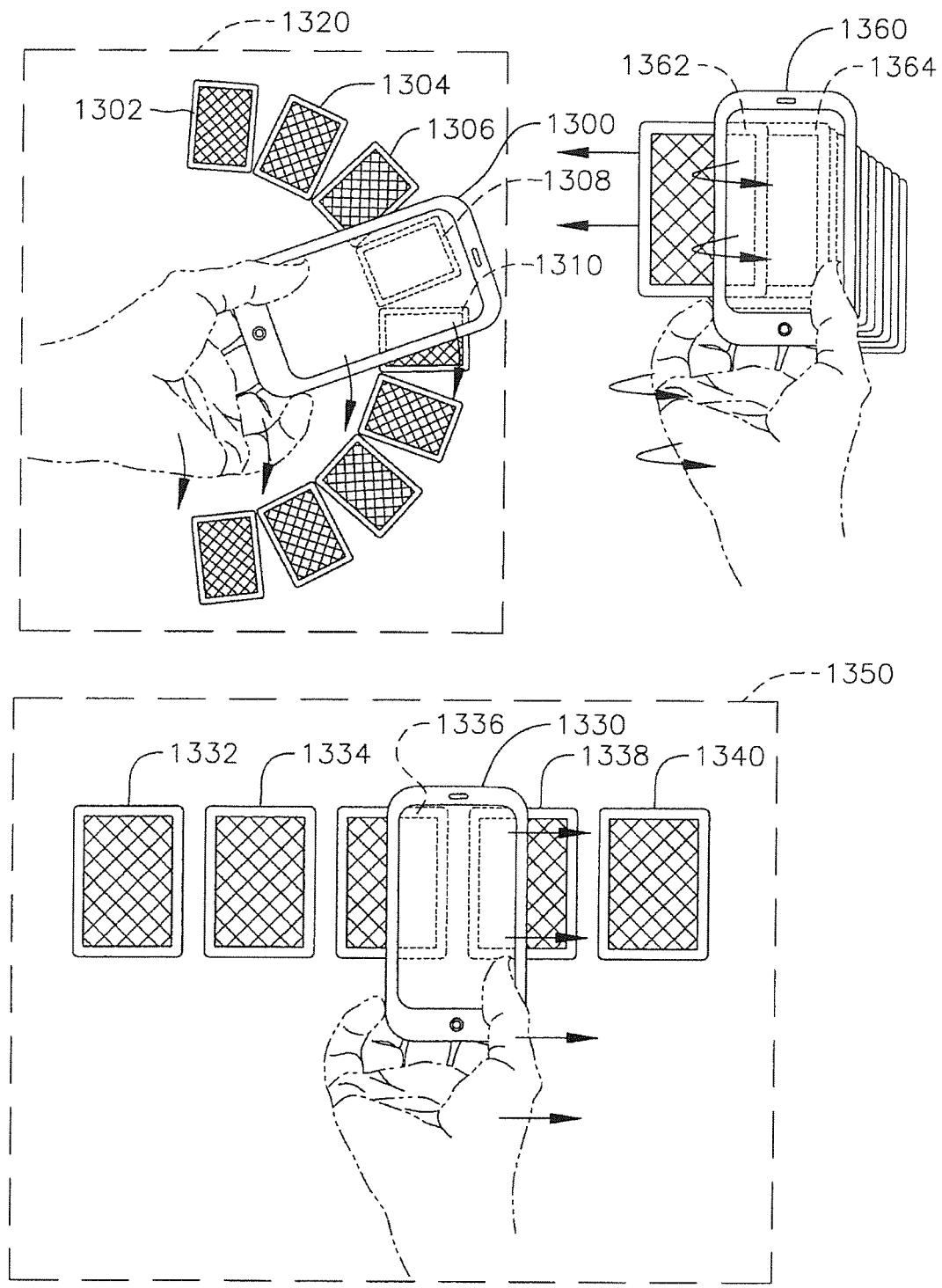
FIG. 13 is a view of navigation and display schemes involving translation or manipulation of a portable computing device.

In an embodiment employing a navigational tilt, when the device navigates from one screen to the next, the visual transition between the screens need not be instantaneous, but may be depicted as the screen being navigated away from sliding off the screen and the screen being navigated toward sliding onto the screen. If this depicted sliding action is in the opposite direction from the tilt motion, this would render the illusion of the device's display being scanned over a virtual display space containing an arc of various screens, as depicted in FIG. 13. Portable computing device 1300 is set to transition approximately four times, from screen 1302 through screens 1304, 1306, and 1308, to screen 1310, as it is tilted through ninety degrees about its screen-normal axis. With the device's screen depicting a sliding transition between the respective screens, the illusion is rendered that the screens are arranged in an arc on a larger virtual display space 1320 behind the device and that the device's display is a viewing window moving over that virtual display space.

The navigation may be sensitive to the direction of the tilt. In one option, after a first screen is transitioned to a second screen by a clockwise tilt of the device through for example ninety degrees, tilting the device back ninety degrees counter-clockwise would transition back from the second screen to the first screen. In another option, a clockwise tilt would trigger a different type of navigation transition, such that tilting the device ninety degrees clockwise would transition from a first screen to a second screen, but tilting the device back ninety degrees counter-clockwise would transition from the second screen to a third screen. The size of the navigational tilt triggering a screen transition need not be the same in the clockwise direction as in the counter-clockwise direction.

The navigation transition brought about by a navigational tilt need not be a full-screen transition, but may be of smaller difference within a particular screen, such as changing only a portion of the screen, or setting a control on the screen into a different state. This may have the effect, for example, of moving through a the options of a "picker" wheel, which would be particularly intuitive for the user if the tilt that triggers the picker's movement is not around a screen normal axis, but instead around an axis that is aligned with the hypothetical rotational axis of the displayed picker, thus imparting the illusion that the picker is fixed in space and the physical device is tied to the selection highlight as it moves around the picker.

In another embodiment, a "navigational slide" is employed instead of a navigational tilt. In this embodiment, a first screen transitions to a second screen when the portable computing device is translated or slid in a particular direction by a certain amount. As with a navigational tilt, if the screen does not display the transition instantaneously but depicts it as the screen being navigated away from sliding off the screen and the screen being navigated toward sliding onto the screen, the illusion is rendered of the device's display being scanned over a virtual display space containing a line of various screens, as depicted in FIG. 13. Portable computing device 1330 is set to transition multiple times, from screen 1332 through screens 1334, 1336, and 1338, to screen 1340, as the devices is translated from left to right. With the device's screen depicting a sliding transition between the respective screens, the illusion is rendered that the screens are arranged in a line on a larger virtual display space 1350 behind the device and that the device's display is a viewing window sliding across that virtual display space.

The navigation transition from a navigational slide may initiate a different navigational change or a different type of navigational change in each of the four directions up, down, left and right with respect to the screen, or with a greater number of directions, such as eight "compass points" with respect to the screen. As with navigational tilt, it may be the case that if a translation to the right transitions from a first screen to a second screen, a translation back to the left will transition back from the second screen to the first screen, but this need not necessarily be so. Also as with directional tilt, the sensitivity of the navigational slide, i.e. how far the device must be translated to cause a navigation transition, may be different in different directions.

A navigational slide need not be in the directions on the plane of the device's display, but may also be in a direction normal to the screen. In this way, as the device whose screen is facing the user is brought toward or away from the user, the screen may transition once or several times. If several transitions are implemented during such a device translation, this may impart the illusion of the device moving through multiple layers and displaying a screen associated with each layer as the device crosses it.

As with a navigational tilt, a navigation transition brought about by a navigational slide need not be a full-screen transition, but may be of smaller difference within a particular screen, such as changing only a portion of the screen, or setting a control on the screen into a different state. This may have the effect, for example, of moving a slider bar, and if the slider bar indicator moves in the opposite direction of the device translation, this may impart thus impart the illusion that the slider bar indicator is fixed in space and the device is tied to the slider bar behind the indicator it moves underneath the static indicator.

In another embodiment, a "navigational snap" is employed instead of a navigational tilt or navigational slide. A snap movement for this purpose is somewhat similar to shaking the device, but a snap can be delivered with a single accelerative movement of the device in a particular direction followed by an abrupt deceleration and perhaps a partial or full movement back in the opposite direction. As with a navigational tilt or navigational slide, a navigational snap causes a navigational transition from one screen to another screen. Also as with a navigational tilt or navigational slide, a navigational snap may initiate a different navigational change or a different type of navigational change when executed in each of the four directions up, down, left and right with respect to the screen, or with a greater number of directions, such as eight "compass points" with respect to the screen, or with a snap normal to the screen, forward or back, and a second snap in an opposite direction may but need not restore the screen transitioned away from in a first snap. Further as with a navigational tilt or navigational slide, a navigation transition brought about by a navigational snap need not be a full-screen transition, but may be of smaller difference within a particular screen, such as changing only a portion of the screen, or setting a control on the screen into a different state. Similar to a navigational tilt or navigational slide, if the device's screen does not display the navigational transition instantaneously but depicts it as the screen being navigated away from sliding off the screen to reveal the screen being navigated toward, the illusion is rendered of "snapping away" a screen, as depicted in FIG. 13. When portable computing device 1360 is snapped initially to the left and then recovered to the right, screen 1362 is depicted as sliding to the left and off the screen to reveal screen 1364, as though the screen were a card that were being snapped off the top of a deck of cards to reveal the card underneath it.

Other Embodiments

Although limited embodiments of the present invention have been specifically described and illustrated, many modifications, combinations, and variations will be apparent to those skilled in the various relevant arts. Accordingly, it is to be understood that a user control system for therapeutic wellness devices constructed according to the principles of this invention may be embodied other than as specifically described herein. The invention is also defined in the following claims.

What is claimed is:

1. A system comprising:
   a therapeutic wellness device; and
   a remote control capable of connection to a data communications network and configured to display one or more graphical representations of a human body, wherein at least one of the one or more graphical representations comprises an outline of a single human body having a plurality of separately selectable therapeutic regions positioned within the outline of the single human body, wherein the remote control comprises:
      a processor; and
      a memory coupled to the processor, wherein the memory stores instructions that, when executed by the processor, cause the processor to:
         provide a first command to the therapeutic wellness device to initiate a therapy activity in a first region of the therapeutic wellness device in response to one of the separately selectable therapeutic regions being touched by a user, wherein the first region of the therapeutic wellness device corresponds to the one of the separately selectable therapeutic regions touched by the user, wherein the remote control is capable of transmitting data between the therapeutic wellness device and the remote control over the data communication network;
         receive user identification data for identifying the user; and
         provide a second command to the therapeutic wellness device based on the user identification data,
      wherein the remote control is portable and the data communications network is wireless,
      wherein the remote control is configured to retain data pertaining to the user,
      wherein the retained data comprises a preference of the user regarding an operation of the at least one therapeutic wellness device, and
      wherein the remote control is configured to select an item of therapy to suggest to the user.

2. The system of claim 1, wherein the remote control comprises a general purpose computer.

3. The system of claim 1, wherein the remote control comprises a software application capable of directing control of the therapeutic wellness device.

4. The system of claim 1, wherein the remote control comprises a means for graphically interacting with the user.

5. The system of claim 1, wherein the therapeutic wellness device is a massage chair.

6. The system of claim 1, wherein the data communication network is wireless.

7. The system of claim 1, wherein the therapeutic wellness device is capable of transmitting data over the data communication network.

8. The system of claim 7, wherein data capable of being transmitted over the data communication network pertain to a condition of the therapeutic wellness device.

9. The system of claim 8, wherein data capable of being transmitted over the data communication network pertain to a usage of the therapeutic wellness device.

10. The system of claim 1, comprising software residing in the therapeutic wellness device that is capable of being modified by data transmitted across the data communication network.

11. A system comprising:
    a remote control capable of connection to a data communications network and programmed to direct the control at least one therapeutic wellness device across the data communications network and configured to display one or more graphical representations of a human body, wherein at least one of the one or more graphical representations comprises an outline of a single human body having a plurality of separately selectable therapeutic regions positioned within the outline of the single human body,
    wherein the remote control comprises:
       a processor; and
       a memory coupled to the processor, wherein the memory stores instructions that, when executed by the processor, cause the processor to:
          provide a command to the therapeutic wellness device to initiate a therapy activity in a region of the at least one therapeutic wellness device in response to one of the separately selectable therapeutic regions being touched by a user, wherein the region of the at least one therapeutic wellness device corresponds to the one of the separately selectable therapeutic regions touched by the user
          receive user identification data for identifying the user; and
          provide a second command to the therapeutic wellness device based on the user identification data,
       wherein the remote control is configured to retain data pertaining to the user,
       wherein the retained data comprises a preference of the user regarding an operation of the at least one therapeutic wellness device,
       wherein the remote control is portable and the data communications network is wireless, and
       wherein the remote control is configured to select an item of therapy to suggest to the user.

12. The system of claim 11, wherein the remote control is configured to maintain a data link with the at least one therapeutic wellness device when the remote control is brought into proximity with the at least one therapeutic wellness device.

13. The system of claim 11, wherein the remote control is configured to maintain a data link with the at least one therapeutic wellness device.

14. The system of claim 11, wherein the remote control is configured to convert therapeutic wellness device model-independent information into data compatible with the at least one therapeutic wellness device.

15. The system of claim 11, wherein time of day affects the selection of the item of therapy to suggest to the user.

16. The system of claim 11, wherein the instructions further cause the processor to display an interactive graphical user interface on the remote control.

17. The system of claim 16, wherein the interactive graphical user interface is configured to communicate intended benefits from at least one program that is available for selection by the user.

18. The system of claim 11, wherein the therapeutic wellness device is a massage chair.

19. A method of controlling a therapeutic wellness device comprising:
    obtaining, across a data communications network capable of permitting data communication between the therapeutic wellness device and a remote control capable of connection to the data communications network, a program comprising instructions capable of being used in conjunction with directing the control of the therapeutic wellness device, wherein the instructions comprise:
    displaying, by a processor, one or more graphical representations of a human body, wherein at least one of the one or more graphical representations comprises an outline of a single human body having a plurality of separately selectable therapeutic regions positioned within the outline of the single human body on the remote control;

sensing, by the processor, one of the separately selectable therapeutic regions being touched by a user of the remote control; and providing, by the processor, a command to the therapeutic wellness device to initiate a therapy activity in a region of the therapeutic wellness device corresponding to the one of the separately selectable therapeutic regions touched by the user;

receiving, by the processor, over a wide area network, a sequence for the therapy activity for the region of the therapeutic wellness device corresponding to the one of the separately selectable therapeutic regions touched by the user;

providing, by the processor, the sequence for the therapy activity to the therapeutic wellness device;

receiving, by the processor, user identification data for identifying the user; and providing, by the processor, a second command to the therapeutic wellness device based on the user identification data, wherein the remote control is portable and the data communications network is wireless, wherein the remote control is configured to retain data pertaining to the user, wherein the retained data comprises a preference of the user regarding an operation of the at least one therapeutic wellness device, and wherein the remote control is configured to select an item of therapy to suggest to the user.

20. The method of claim 19, wherein the remote control is a general purpose computer and the program is selected from a plurality of programs made available by the general purpose computer over the data communications network.

21. The method of claim 19, wherein the program is obtained from a website.

22. The method of claim 19, wherein the program is obtained from a medical provider.

23. The method of claim 19, wherein the program is obtained from a source identified with providing programs that comprise instructions capable of being used in conjunction with controlling at least one model of therapeutic wellness device.

24. The method of claim 19, wherein the program is obtained from a source of supply of at least one model of therapeutic wellness device.

25. The method of claim 19, wherein the therapeutic wellness device is a massage chair.

26. The system of claim 1, wherein the instructions further cause the processor to:
display an interface configured to enable the user to select a sequence of therapy activities.

27. The system of claim 1, wherein the instructions further cause the processor to:
sense a squeezing motion or a spreading motion by the user on the remote control; and
adjust a size of the graphical representation of the human body displayed on the remote control.

28. The system of claim 1, wherein the instructions further cause the processor to display a graphical timer indicating a duration of the therapy activity.

29. The system of claim 1, wherein the instructions further cause the processor to:
sense a squeezing motion or a spreading motion by the user on the remote control; and
provide a second command to the therapeutic wellness device to adjust a vertical or horizontal span of the therapy activity.

30. The system of claim 1, wherein the instructions further cause the processor to:
receive, over a wide area network, a sequence for the therapy activity for the region of the therapeutic wellness device corresponding to the one of the separately selectable therapeutic regions touched by the user; and
provide the sequence for the therapy activity to the therapeutic wellness device.

31. The system of claim 1, wherein the instructions further cause the processor to display a multimedia presentation related to the therapy activity.

32. The system of claim 1, wherein the remote control comprises a display screen and the remote control is configured to display the graphical representation of the human body comprising the plurality of separately selectable therapeutic regions on the display screen.

33. A method of controlling a therapeutic wellness device comprising:
displaying one or more graphical representations of a human body on a remote control in electronic communication with the therapeutic wellness device over a data communication network, wherein at least one of the one or more graphical representations comprises an outline of a single human body having a plurality of separately selectable regions positioned within the outline of the single human body;
sensing one of the separately selectable regions being touched by a user of the remote control; and
initiating a therapy activity in a region of the therapeutic wellness device corresponding to the one of the separately selectable regions touched by the user,
receiving user identification data for identifying the user; and
providing a second command to the therapeutic wellness device based on the user identification data,
wherein the remote control is portable and the data communication network is wireless,
wherein the remote control is configured to retain data pertaining to the user,
wherein the retained data comprises a preference of the user regarding an operation of the at least one therapeutic wellness device, and
wherein the remote control is configured to select an item of therapy to suggest to the user.

34. A computer program product usable with a programmable computer processor including a computer readable program code embodied in a non-transitory computer usable medium, the computer readable program code adapted to implement a method of controlling a therapeutic wellness device, the computer program product comprising:
obtaining, across a data communication network capable of permitting data communication between the therapeutic wellness device and a remote control capable of connection to the data communication network, a program comprising instructions capable of being used in conjunction with directing the control of the therapeutic wellness device, wherein the instructions comprise:
displaying one or more graphical representations of a human body, wherein at least one of the one or more graphical representations comprises an outline of a single human body having a plurality of separately selectable therapeutic regions positioned within the outline of the single human body on the remote control;

sensing one of the separately selectable therapeutic regions being touched by a user of the remote control;

providing a command to the therapeutic wellness device to initiate a therapy activity in a region of the therapeutic wellness device corresponding to the one of the separately selectable therapeutic regions touched by the user, wherein the remote control is portable and the data communication network is wireless;

receiving over a wide area network, a sequence for the therapy activity for the region of the therapeutic wellness device corresponding to the one of the separately selectable therapeutic regions touched by the user;

providing the sequence for the therapy activity to the therapeutic wellness device;

receiving user identification data for identifying the user; and providing a second command to the therapeutic wellness device based on the user identification data, wherein the remote control is portable and the data communications network is wireless, wherein the remote control is configured to retain data pertaining to the user, wherein the retained data comprises a preference of the user regarding an operation of the at least one therapeutic wellness device, and wherein the remote control is configured to select an item of therapy to suggest to the user.

35. A computer program product usable with a programmable computer processor including a computer readable program code embodied in a non-transitory computer usable medium, the computer readable program code adapted to implement a method of controlling a therapeutic wellness device, the computer program product comprising:

displaying one or more graphical representations of a human body on a remote control in electronic communication with the therapeutic wellness device over a data communication network, wherein at least one of the one or more graphical representations comprises an outline of a single human body having a plurality of separately selectable regions positioned within the outline of the single human body;

sensing one of the separately selectable regions being touched by a user of the remote control;

initiating a therapy activity in a region of the therapeutic wellness device corresponding to the one of the separately selectable regions touched by the user, wherein the remote control is portable and the data communication network is wireless;

receiving user identification data for identifying the user; and providing a second command to the therapeutic wellness device based on the user identification data, wherein the remote control is portable and the data communication network is wireless, wherein the remote control is configured to retain data pertaining to the user, wherein the retained data comprises a preference of the user regarding an operation of the at least one therapeutic wellness device, and wherein the remote control is configured to select an item of therapy to suggest to the user.

36. The system of claim 1, wherein the data communication network is implemented using a short-range wireless connection.

37. The system of claim 1, wherein the data communication network is implemented using a Bluetooth standard wireless connection.

* * * * *